(12) United States Patent
Sabbah

(10) Patent No.: US 7,875,017 B2
(45) Date of Patent: Jan. 25, 2011

(54) CARDIAC REPAIR, RESIZING AND RESHAPING USING THE VENOUS SYSTEM OF THE HEART

(75) Inventor: Hani N. Sabbah, Waterford, MI (US)

(73) Assignee: Henry Ford Health System, Detriot, MI (US)

( * ) Notice: Subject to any disclaimer, the term of this patent is extended or adjusted under 35 U.S.C. 154(b) by 0 days.

(21) Appl. No.: 12/082,368

(22) Filed: Apr. 10, 2008

(65) Prior Publication Data

US 2008/0269720 A1  Oct. 30, 2008

Related U.S. Application Data

(60) Provisional application No. 60/922,930, filed on Apr. 11, 2007, provisional application No. 60/934,042, filed on Jun. 11, 2007, provisional application No. 60/934,109, filed on Jun. 11, 2007, provisional application No. 60/934,111, filed on Jun. 11, 2007.

(51) Int. Cl.
*A61M 31/00* (2006.01)
(52) U.S. Cl. .................................. 604/508; 604/57
(58) Field of Classification Search ............ 604/508, 604/511, 522, 57
See application file for complete search history.

(56) References Cited

U.S. PATENT DOCUMENTS

| | | | |
|---|---|---|---|
| 5,328,471 A | 7/1994 | Slepian | |
| 6,063,061 A | 5/2000 | Wallace et al. | |
| 6,096,021 A | 8/2000 | Helm et al. | |
| 6,132,451 A | 10/2000 | Payne et al. | |

(Continued)

FOREIGN PATENT DOCUMENTS

EP  1707233 A2  10/2006

(Continued)

OTHER PUBLICATIONS

U.S. Appl. No. 60/813,814, Lee, et al.

(Continued)

*Primary Examiner*—Kevin C Sirmons
*Assistant Examiner*—Bradley J Osinski
(74) *Attorney, Agent, or Firm*—David H. Carroll

(57) ABSTRACT

Structurally supportive material is implanted or injected into cardiac veins as discrete masses at various sites in the cardiac venous system to reinforce the myocardium for the purpose of preventing, moderating, stopping or reversing negative cardiac remodeling due to various adverse cardiac conditions, both acute and chronic, or for the purpose of treating localize anomalies of the heart, or for both purposes. The sites may be arranged in a pattern about one or more chambers of the heart such that the masses cooperatively reduce stress in the chamber wall and reduce chamber size. Some patterns also cause a beneficial global reshaping of the chamber. These changes occur quickly and are sustainable, and have a rapid and sustainable therapeutic effect on cardiac function. Patterns of distribution of discrete masses in the heart for global resizing and reshaping may also be used as is or augmented by supplemental patterns to treat localized conditions such as myocardial infarctions and overt aneurysm of the ventricular wall as typically forms in response to large transmural myocardial infarctions. These techniques may also be used to treat localized conditions that may not yet have progressed to cardiomyopathy.

37 Claims, 20 Drawing Sheets

U.S. PATENT DOCUMENTS

| | | |
|---|---|---|
| 6,238,406 B1 | 5/2001 | Ellis et al. |
| 6,334,968 B1 | 1/2002 | Shapiro et al. |
| 6,360,749 B1 | 3/2002 | Jayaraman |
| 6,425,918 B1 | 7/2002 | Shapiro et al. |
| 6,508,824 B1 | 1/2003 | Flaherty et al. |
| 6,566,406 B1 | 5/2003 | Pathak et al. |
| 6,575,932 B1 | 6/2003 | O'Brien et al. |
| 6,585,716 B2 | 7/2003 | Altman |
| 6,689,103 B1 | 2/2004 | Palasis |
| 6,730,016 B1 | 5/2004 | Cox et al. |
| 6,808,488 B2 | 10/2004 | Mortier et al. |
| 6,887,974 B2 | 5/2005 | Pathak |
| 6,908,424 B2 | 6/2005 | Mortier et al. |
| 6,926,689 B2 | 8/2005 | Scheule |
| 6,962,588 B2 | 11/2005 | Sauvageau et al. |
| 7,031,775 B2 | 4/2006 | Soykan et al. |
| 7,044,905 B2 | 5/2006 | Vidlund et al. |
| 7,094,230 B2 | 8/2006 | Flaherty et al. |
| 7,189,199 B2 | 3/2007 | McCarthy et al. |
| 7,226,440 B2 | 6/2007 | Gelfand et al. |
| 7,670,329 B2 | 3/2010 | Flaherty et al. |
| 2002/0042554 A1 | 4/2002 | Alferness et al. |
| 2002/0077687 A1 | 6/2002 | Ahn |
| 2002/0106793 A1 | 8/2002 | West et al. |
| 2002/0169360 A1 | 11/2002 | Taylor et al. |
| 2002/0188170 A1 | 12/2002 | Santamore et al. |
| 2003/0060415 A1 | 3/2003 | Hung |
| 2003/0078671 A1 | 4/2003 | Lesniak et al. |
| 2003/0104568 A1 | 6/2003 | Lee |
| 2003/0119718 A1 | 6/2003 | Wolff et al. |
| 2003/0211793 A1 | 11/2003 | Bell et al. |
| 2004/0002626 A1 | 1/2004 | Feld et al. |
| 2004/0005295 A1 | 1/2004 | Lee et al. |
| 2004/0023842 A1 | 2/2004 | Pathak et al. |
| 2004/0030286 A1 | 2/2004 | Altman |
| 2004/0102759 A1 | 5/2004 | Altman et al. |
| 2004/0133063 A1 | 7/2004 | McCarthy et al. |
| 2004/0158123 A1* | 8/2004 | Jayaraman .................. 600/37 |
| 2004/0180043 A1 | 9/2004 | Sabbah et al. |
| 2004/0208845 A1 | 10/2004 | Michal et al. |
| 2004/0214760 A1 | 10/2004 | Gupta et al. |
| 2004/0267083 A1 | 12/2004 | McCarthy et al. |
| 2005/0003010 A1 | 1/2005 | Cohen et al. |
| 2005/0004428 A1 | 1/2005 | Cox et al. |
| 2005/0008628 A1 | 1/2005 | Feld et al. |
| 2005/0065396 A1 | 3/2005 | Mortier et al. |
| 2005/0080402 A1 | 4/2005 | Santamore et al. |
| 2005/0131277 A1 | 6/2005 | Schweich, Jr. et al. |
| 2005/0143620 A1 | 6/2005 | Mortier et al. |
| 2005/0271631 A1 | 12/2005 | Lee et al. |
| 2006/0002898 A1 | 1/2006 | Lee et al. |
| 2006/0041243 A1 | 2/2006 | Nayak et al. |
| 2006/0083717 A1 | 4/2006 | Lee et al. |
| 2006/0083721 A1 | 4/2006 | Cohen et al. |
| 2006/0111361 A1 | 5/2006 | Blackburn et al. |
| 2006/0149123 A1 | 7/2006 | Vidlund et al. |
| 2006/0233850 A1 | 10/2006 | Michal |
| 2006/0241334 A1 | 10/2006 | Dubi et al. |
| 2006/0253068 A1 | 11/2006 | van Bilsen et al. |
| 2006/0276683 A1 | 12/2006 | Feld et al. |
| 2007/0014784 A1 | 1/2007 | Nayak et al. |
| 2007/0027487 A1 | 2/2007 | Mika et al. |
| 2007/0042016 A1 | 2/2007 | Nayak et al. |
| 2007/0093748 A1 | 4/2007 | Nayak et al. |
| 2007/0112244 A1 | 5/2007 | McCarthy et al. |
| 2007/0172472 A1 | 7/2007 | Nayak |
| 2008/0065046 A1 | 3/2008 | Sabbah et al. |
| 2008/0065048 A1 | 3/2008 | Sabbah et al. |
| 2008/0069801 A1 | 3/2008 | Lee et al. |
| 2009/0259210 A1 | 10/2009 | Sabbah |

FOREIGN PATENT DOCUMENTS

| | | |
|---|---|---|
| WO | 9850079 | 11/1998 |
| WO | 9948545 | 9/1999 |
| WO | 0107568 A2 | 2/2001 |
| WO | 0110313 A1 | 2/2001 |
| WO | 02087481 A1 | 11/2002 |
| WO | 03043507 A2 | 5/2003 |
| WO | 03080798 A2 | 10/2003 |
| WO | 2004050013 A2 | 6/2004 |
| WO | 2006019728 A2 | 2/2006 |
| WO | 2007024414 A2 | 3/2007 |
| WO | 2008127607 A2 | 10/2008 |

OTHER PUBLICATIONS

U.S. Appl. No. 60/922,930, Sabbah.

U.S. Appl. No. 60/934,042, Ahmann, et al.

U.S. Appl. No. 60/934,109, Ahmann, et al.

U.S. Appl. No. 60/934,111, Cohen, et al.

U.S. Appl. No. 61/123,700, Sabbah.

Kashem, Abul, et al., CardioClasp: A New Passive Device to Re-Shape Cardiac Enlargement, ASAIO Journal, 2002.

Kong, H., et al., Controlling Material Properties of Ionically Cross-linked Alginate Hydrogels by Varying Molecular Weight Distribution, Mat. Res. Soc. Symp. Proc., vol. 711, 2002, pp. GG5.7.1-GG5.7.4.

Lenfant, C., Cardiovascular Research: An NIH Perspective, Cardiovascular Surgery, vol. 5, No. 1, 1997, pp. 4-5.

Rastogi, Sharad, et al., Reversal of Maladaptive Gene Program in Left Ventricular Myocardium of Dogs With Heart Failure Following Long-Term Therapy with the Acorn Cardiac Support Device, Heart Failure Reviews, vol. 10, 2005, pp. 157-163.

Sabbah, Hani N., Reversal of Chronic Molecular and Cellular Abnormalities Due to Heart Failure by Passive Mechanical Ventrical Containment, Circ. Res., vol. 93, 2003, pp. 1095-1101.

Torrent-Guasp, F., et al., Towards New Understanding of the Heart Structure and Function, European Journal of Cardio-thoracic Surgery, vol., 27, 2005, pp. 191-201.

Wall, Samuel T., et al., Theoretical Impact on the Injection of Material Into the Myocardium: A Finite Element Model Simulation, Circulation AHA 106.657270, Nov. 27, 2006, pp. 1-9.

International Searching Authority / European Patent Office, International Search Report for International Application No. PCT/US2008/004613, Aug. 25, 2009, 4 pages.

International Searching Authority / European Patent Office, Written Opinion of the International Search Authority for International Application No. PCT/US2008/004613, 8 pages.

American Heart Association, 2001 Heart and Stroke Statistical Update, Dallas, Texas: American Heart Association, 2000.

Cohn, J.N., et al., Report of the National Heart, Lung, and Blood Institute Special Emphasis Panel on Heart Failure Research, Circulation, vol. 95, 1997, pp. 766-770.

Kelley St, Malekan R, Gorman JH 3rd, et al., Restraining Infarct Expansion Preserves Left Ventricle Geometry and Function After Acute Anteroapical Infarction, Circulation 1999, vol. 99, pp. 135-142.

Lenfant, C., Fixing the Failing Heart, Circulation, vol. 95, 1997, pp. 771-772.

Buckberg, Gerald D., Tenth Restore Group Meeting Overview; European Journal of Cardio-Thoracic Surg., vol. 29, 2006, pp. 8213-8215.

Burkhoff, Daniel, New Heart Failure Therapy: The Shape of Things to Come?, J. Thoracic Cardiovascular Surg., vol. 123, No. 3, Mar. 2003, pp. S50-S53.

Christman, Karen L., et al., Injectable Fibrin Scaffold Improves Cell Transplant Survival, Reduces Infarct Expansion, and Induces Neovasculture Formation in Ischemic Myocardium, J. American Col. of Cardiology, vol. 44, No. 3, Aug. 4, 2004, pp. 654-660.

Christman, Karen L., et al., Fibrin Glue Alone and Skeletal Myoblasts in a Fibrin Scaffold Preserve Cardiac Function After Myocardial Infarction, Tissue Engineering, vol. 10, No. 3/4, 2004, pp. 403-409.

Guccione, Julius M., et al., Myosplint Decreases Wall Stress Without Depressing Function in the Failing Heart: A Finite Element Study, The Annals of Thoracic Surgery, vol. 76, 2003, pp. 1171-1180.

Huang, Ngan F., et al., Injectable Biopolymers Enhance Angiogenesis After Myocardial Infarction, Tissue Engineering, vol. 11, No. 11/12, 2005, pp. 1860-1866.

International Searching Authority / European Patent Office, International Search Report, International Patent Application No. PCT/US2007/019575, Feb. 16, 2009, 16 pages.

International Searching Authority / European Patent Office, International Search Report, International Patent Application No. PCT/US2009/002258, Aug. 18, 2009, 8 pages.

International Searching Authority / European Patent Office, Written Opinion of the International Searching Authority, International Patent Application No. PCT/US2007/019575, Feb. 16, 2009, 6 pages.

International Searching Authority / European Patent Office, Written Opinion of the International Searching Authority, International Patent Application No. PCT/US2009/002258, Aug. 18, 2009, 12 pages.

Kofidis, Theo, et al., Injectable Bioartificial Myocardial Tissue for Large-Scale Intramural Cell Transfer and Functional Recovery of Injured Heart Muscle, J. Thoracic Cardiovascular Surg., vol. 128, No. 4, Oct. 2004, pp. 571-578.

Lee, Randall, et al., Method and Apparatus for Using Biopolymer-Based Beads and Hydrogels for Cardiac Repair and Reconstruction and for Modification of Electrical Conduction in the Heart, U.S. Appl. No. 60/813,184, filed Jun. 13, 2006, 296 pages.

Lee, Randall, et al., Intramyocardial Patterning for Cardiac Reshaping and Remodeling, U.S. Appl. No. 60/843,475, filed Sep. 8, 2006, 157 pages.

Mann, Douglas L., Left Ventricular Size and Shape: Determinants of Mechanical Signal Transduction Pathways, Heart Failure Rev., vol. 10, 2005, pp. 95-100.

McCarthy, Patrick M. et al., Device-Based Change in Left Ventricular Shape: A New Concept for the Treatment of Dilated Cardiomyopathy, J. Thoracic Cardiovascular Surg., vol. 122, No. 3, 2001, pp. 482-490.

Ratcliffe, Mark, B., et al., Radio Frequency Heating of Chronic Ovine Infarct Leads to Sustained Infarct Area and Ventricular Volume Reduction, J. Thoracic Cardiovascular Surg., vol. 119, No. 6, Jun. 2000, pp. 1194-1204.

Sabbah, Hani N., The Cardiac Support Device and the Myosplint: Treating Heart Failure by Targeting Left Ventricular Size and Shape, Ann. Thorac Surg., vol. 75, 2003, S13-S19.

Sabbah, Hani N., Global Left Ventricular Remodeling With the Acorn Cardiac Support Device: Hemodynamic and Angiographic Findings in Dogs With Heart Failure, Heart Failure Rev., vol. 10, 2005, pp. 109-115.

Sabbah, Hani N., et al., Reply to Office Action, U.S. Appl. No. 11/899,962, filed Apr. 13, 2009, 9 pages.

Sabbah, Hani N., et al., Reply to Office Action, U.S. Appl. No. 11/899,962, filed Oct. 5, 2009, 13 pages.

US Patent and Trademark Office, Office Action, U.S. Appl. No. 11/899,962, filed Oct. 15, 2008, 28 pages.

US Patent and Trademark Office, Office Action, U.S. Appl. No. 11/899,962, filed Jun. 4, 2009, 14 pages.

US Patent and Trademark Office, Office Action, U.S. Appl. No. 11/899,962, filed Dec. 22, 2009, 37 pages.

Victal, Octavio, et al., Left Ventricular Volume Reduction by Radiofrequency Heating of Chronic Myocardial Infarction in Patients With Congestive Heart Failure, Circulation, vol. 105, 2002, pp. 1317-1322.

Sabbah et al., Reply to Office Action, U.S. Appl. No. 11/899,962, filed Jun. 22, 2010, 16 pages.

US Patent and Trademark Office, Office Action, U.S. Appl. No. 11/899,962, filed Aug. 24, 2010, 35 pages.

European Patent Office, Office Action, European Patent Application No. 08 742 708.4, Mar. 11, 2010, 4 pages.

Gill et al., Cardiac Diastolic Dysfunction in Conscious Dogs With Heart Failure Induced by Chronic Coronary Microembolization, Am J Physiol Heart Circ Physiol, vol. 291, Dec. 2006, pp. H3154-H3158.

Henry Ford Health System, Reply to Office Action, European Patent Application No. 08 742 708.4, Sep. 2, 2010, 5 pages.

Henry Ford Health System, Voluntary Amendment, European Patent Application No. 08 742 708.4, Dec. 7, 2009, 9 pages.

International Searching Authority/EPO, International Search Report, International Patent Application No. PCT/US2007/019496, Jan. 28, 2008, 6 pages.

International Searching Authority/EPO, Written Opinion of the International Searching Authority, International Patent Application No. PCT/US2007/019496, Jan. 28, 2008, 6 pages.

Kono et al., Left Atrial Contribution to Ventricular Filling During the Course of Evolving Heart Failure, Circulation, vol. 86, No. 4, Oct. 1992, pp. 1317-1322.

\* cited by examiner

CARDIAC REPAIR, RESIZING AND RESHAPING USING THE VENOUS SYSTEM OF THE HEART

CROSS-REFERENCE TO RELATED APPLICATIONS

This application claims the benefit of U.S. Provisional Patent Application Ser. No. 60/922,930 filed Apr. 11, 2007 (Hani N. Sabbah, "Cardiac Shaping and Remodeling Using the Venous System of the Heart,"), U.S. Provisional Patent Application Ser. No. 60/934,042 filed Jun. 11, 2007 (Frank A. Ahmann et al., Cardiac Remodeling Using a Viscous Scaffolding Agent Injectate for Controlled Dispersion in the Cardiac Venous System,"), U.S. Provisional Patent Application Ser. No. 60/934,109 filed Jun. 11, 2007 (Frank A. Ahmann et al., Cardiac Remodeling Using a Particulate Scaffolding Agent Injectate for Controlled Dispersion in the Cardiac Venous System,"), U.S. Provisional Patent Application Ser. No. 60/934,111 filed Jun. 11, 2007 (Raymond W. Cohen et al., Use of the Cardiac Venous System for Introducing Drug-Eluting Materials into the Heart,"), all of which hereby are incorporated herein in their entirety by reference thereto.

BACKGROUND OF THE INVENTION

1. Field of the Invention

The present invention relates to treatment of cardiac conditions in living beings, and more particularly to global cardiac resizing and reshaping using the venous system of the heart.

2. Description of Related Art

Cardiovascular disease ("CVD") is the leading cause of death in the United States; see, e.g., C. Lenfant, Fixing the Failing Heart, Circulation, Vol. 95, 1997, pages 771-772; American Heart Association, Heart and Stroke Statistical Update, 2001; C. Lenfant, Cardiovascular Research: An NIH Perspective, Cardiovasc. Surg., Vol. 5, 1997; pages 4-5; J. N. Cohn et al., Report of the National Heart, Lung, and Blood Institute Special Emphasis Panel on Heart Failure Research, Circulation, Vol. 95, 1997, pages 766-770.

Heart failure ("HF") is generally defined as a change in the pumping function of the heart accompanied by typical signs or symptoms. These symptoms typically include shortness of breath or fatigue. Heart failure is a syndrome of ventricular dysfunction in which both ventricles are usually involved to some extent. Left ventricular failure typically causes shortness of breath and fatigue, and right ventricular failure typically causes peripheral and abdominal fluid accumulation. Heart failure is a progressive disorder whereby the hemodynamic and symptomatic states of the patient worsen over time despite the absence of clinically apparent adverse events. The symptomatic deterioration is often accompanied by progressive left ventricular ("LV") chamber remodeling, a process characterized globally by changes in LV chamber size and shape and, at the cellular level, by ongoing loss of cardiomyocytes, myocyte hypertrophy and interstitial fibrosis. Myocyte loss, hypertrophy and accumulation of collagen in the interstitial compartment are important determinants of progressive LV dysfunction, while increased LV size and chamber sphericity and annular dilation secondary to LV systolic dysfunction and dilation are major determinants of functional mitral regurgitation ("MR"). MR is incompetency of the mitral valve causing flow from the left ventricle (LV) into the left atrium during systole, and depending on its severity can have a major impact on reducing LV stroke output which is already impaired in heart failure. Progressive LV dilation can also lead to LV wall stress and myocardial stretch. Increased LV wall stress leads to increased myocardial oxygen consumption, and myocardial stretch can activate stretch response proteins that may play an important role in the development of maladaptive cardiomyocyte hypertrophy. LV dilation and increased LV sphericity are also sensitive indicators of poor long-term outcome.

For these reasons, preventing or reversing remodeling has emerged as desirable in the treatment of cardiomyopathy. Cardiomyopathy is a general term for disease of heart muscle regardless of the underlying etiology, which may be, for example, ischemic, hypertensive, dilated, hypertrophic, infiltrative, restrictive, viral, postpartum, valvular, or idiopathic. Cardomyopathy typically results in heart failure. Examples of various types of cardiomyopathy are as follows. Cor pulmonale is right ventricular enlargement secondary to a lung disorder that produces pulmonary artery hypertension. Right ventricular failure may follow. Dilated congestive cardiomyopathy is myocardial dysfunction producing heart failure in which ventricular dilation and systolic dysfunction predominate. Hypertrophic cardiomyopathy is a congenital or acquired disorder characterized by marked ventricular hypertrophy with diastolic dysfunction but without increased afterload. Examples include valvular aortic stenosis, coarctation of the aorta, and systemic hypertension. Restrictive cardiomyopathy is characterized by noncompliant ventricular walls that resist diastolic filling. Although the left ventricle is most commonly affected, both ventricles may be affected.

At the present time, the most effective treatment for patients in end-stage heart failure is heart transplantation. However, given the chronic shortage of donor hearts, alternate strategies are needed to improve the lives of those with heart failure. Moreover, transplantation is not the most suitable treatment option for patients with milder forms of the disease.

Other treatment approaches include the delivery of drugs to the site of action through the bloodstream, and the injection of cells into ischemic myocardium to improve cardiac function. An example of an approach for treating cardiovascular problems with an intramyocardial scaffolding is disclosed in United States Patent Application Publication No. 2005/0271631, published Dec. 8, 2005 in the name of Lee et al. and entitled "Material compositions and related systems and methods for treating cardiac conditions."

Tissue engineering approaches for cardiac therapy that are generally intended to repair lost or damaged tissue through the use of cellular transplantation and biomaterial scaffolds have also been disclosed. One example of this approach involves suturing fetal cardiomyocyte-seeded alginate gels to the epicardial surface in order to preserve LV function. Another treatment approach involves the use of mechanical external constraints to limit, stop, or even reverse negative left ventricular remodeling. One previously disclosed study included suturing a polymeric mesh to the epicardial surface for the intended purpose of providing an external support to prevent LV dilation and deterioration of LV function post-MI. See Kelley S T, Malekan R, Gorman J H $3^{rd}$ et al., Restraining infarct expansion preserves left ventricle geometry and function after acute anteroapical infarction, Circulation 1999; 99:135-42. Another previously disclosed device that has been investigated provides a plurality of sutures that are implanted in an open-chest procedure across the ventricle under tension to provide a change in the ventricle shape and a decrease in chamber diameter. This trans-cavitary suture network is intended to decrease the radius of the ventricle to thus reduce ventricular wall stress. Another previously disclosed device under clinical investigation is generally a mesh structure that is implanted as a jacket around the heart and adjusted to provide a snug fit during open-chest surgery. It is intended that the jacket restrains the heart from further enlargement. See, for example, Hani N. Sabbah, Reversal of Chronic Molecular and Cellular Abnormalities Due to Heart Failure by Passive Mechanical Ventricular Containment, Circ. Res., Vol. 93, 2003, pages 1095-1101; Sharad Rastogi et al., Reversal of Maladaptive Gene Program in Left Ventricular Myocardium of Dogs with Heart Failure Following Long-Term Therapy with the Acorn Cardiac Support Devide, Heart Failure Reviews, Vol. 10, 2005, pages 157-163. Still another approach being investigated provides a nitinol mesh as a similar external restraining device to that described above; however, the super-elastic system is intended to assist in systolic contraction, and is generally intended for use via thorascopically guided minimally invasive delivery. Still another system being investigated includes a rigid ring that is implanted during open-chest surgery as another external constraining device to the ventricle. This ring is intended to decrease ventricular wall stress and prevent further enlargement of the heart by reducing the radius and modifying the shape of the ventricle. Examples of devices and methods similar to one or more of those discussed above have been disclosed by various companies, including the following: "Acorn;" "Myocor;" "Paracor;" "Cardioclasp;" and "Hearten." The Cardioclasp device is disclosed in an article by Abul Kashem et al., CardioClasp: A New Passive Device to Re-Shape Cardiac Enlargement, ASAIO Journal, 2002.

These techniques have had some success. Long term therapy with the Acorn Cardiac Support Device, for example, was reported to have halted progressive left ventricular dilation and to have improved ejection fraction. This improvement of global LV function was reported as being due to, at least in part, downregulation of stretch response proteins, attenuation of cardiomyocyte hypertrophy, and improvement of sarcoplasmic reticulum calcium cycling. Despite advances in the treatment of heart failure, further improvement in the speed of treatment and reduction of the complexity and intrusiveness of treatment techniques and devices is desirable.

Myocardial infarction ("MI") is a medical emergency in which some of the heart's blood supply is suddenly and severely reduced or cut off, causing the myocardium to die because it is deprived of its oxygen supply. A myocardial infarction may progressively advance into heart failure. Scar tissue formation and aneurysmal thinning of the infarct region often occur in patients who survive myocardial infarctions. It is believed that the death of cardiomyocytes results in negative left ventricular (LV) remodeling which leads to increased wall stress in the remaining viable myocardium. This process results in a sequence of molecular, cellular, and physiological responses which lead to LV dilation. Negative LV remodeling is generally considered an independent contributor to the progression of heart failure.

Despite advances in the treatment of cardiomyopathy and aneurysmal thinning, further improvement in treatment techniques and devices are desirable, especially in conjunction with treatment of heart failure.

BRIEF SUMMARY OF THE INVENTION

One embodiment of the present invention is a kit for treating a heart having a myocardium and a cardiac venous system, comprising a source of biocompatible occluding agent for establishing a therapeutically beneficial structural member within a vein for thickening and strengthening the myocardium of the heart; and an intravenous catheter for delivering the biocompatible occluding agent into a segment of the cardiac venous system. The intravenous catheter comprises a proximal portion for coupling to the source; and a distal portion for introducing the biocompatible occluding agent into the venous segment in a therapeutically effective amount.

Another embodiment of the present invention is a method of treating a heart having a myocardium and a cardiac venous system, comprising identifying a segment of the cardiac venous system for establishing a therapeutically beneficial structural member therein to thicken and strengthen the myocardium of the heart; and introducing biocompatible occluding agent into the segment of the cardiac venous system in a therapeutically effective amount.

Another embodiment of the present invention is a method of treating a heart having a myocardium and a cardiac venous system, comprising identifying a therapeutically beneficial supportive pattern for the myocardium of the heart, the pattern generally spanning a plurality of segments of the cardiac venous system; and introducing a biocompatible occluding agent into the segments of the cardiac venous system in a therapeutically effective amount to establish respective therapeutically beneficial structural members therein for thickening and strengthening the myocardium of the heart in accordance with the pattern.

Another embodiment of the present invention is a method of treating a heart having a dilated chamber and a cardiac venous system, comprising introducing biocompatible occluding agent into a plurality of segments of the cardiac venous system about the chamber and in a therapeutically effective amount to thicken the myocardium, reduce systolic volume of the chamber, and improve function of the chamber.

Another embodiment of the present invention is use of a occluding agent that in a therapeutically effective amount is biologically compatible and effective for establishing a therapeutically beneficial structural member in a segment of the cardiac venous system to thicken and strengthen the myocardium of the heart, for the preparation of a medicament for treating a heart of a patient by administration thereof in a therapeutically effective amount into the segment of the cardiac venous system.

Another embodiment of the present invention is a use of a occluding agent that in a therapeutically effective amount is biologically compatible and effective for establishing a structural member in a segment of the cardiac venous system to thicken and strengthen the myocardium of the heart, for the preparation of a medicament for treating a heart of a patient by administration thereof in a therapeutically effective amount into a plurality of segments of the cardiac venous system lying along a therapeutically beneficial supportive pattern.

DETAILED DESCRIPTION OF THE INVENTION, INCLUDING THE BEST MODE

Structurally supportive material is implanted or injected into cardiac veins as discrete masses occupying various segments of the cardiac venous system to reinforce the myocardium for the purpose of preventing, moderating, stopping or reversing negative cardiac remodeling due to various adverse cardiac conditions, both acute and chronic, or for the purpose of treating localize anomalies of the heart, or for both purposes. Cardiac conditions that may be treated using the techniques described herein include cardiomyopathy, myocardial infarctions, acute myocardial infarctions, arrhythmias, valvular insufficiency, congestive heart failure, mitral regurgitation and other heart valve abnormalities, and other cardiac complications. Kits for treating the cardiac conditions using the techniques described herein are also contemplated.

The myocardium is composed of interlacing bundles of cardiac muscle fibers arranged spirally around the circumference of the heart. These cardiac muscle fibers receive blood through coronary circulation. The coronary arteries branch from the aorta just beyond the aortic valve, and the coronary veins empty into the right atrium. The myocardium is well supplied with a highly distributed system of coronary arteries and veins. Typically, each coronary artery as it courses along the surface of the heart has veins that course alongside it. This is also generally true of the smaller branches of the main coronary arteries and veins, including those that penetrate the thickness of the myocardium and perfuse the deeper layers of the muscle of the heart. Small veins such as venules return the blood to larger cardiac veins. Thus the venous system network of the heart is distributed throughout the thickness of the heart muscle and is present everywhere arteries are present.

Figure 1A:
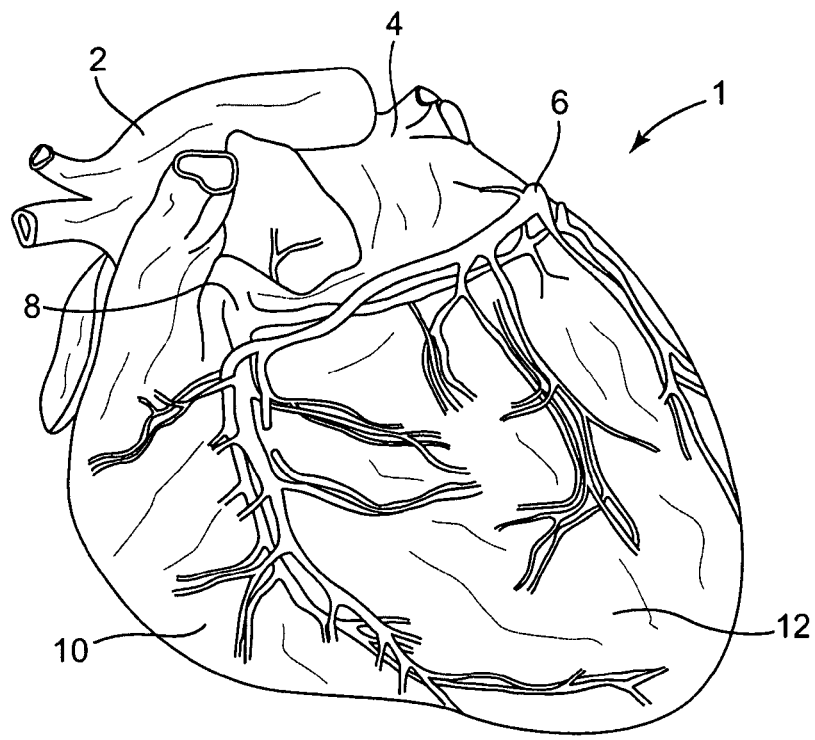
FIG. 1A is a anterior view of the heart.
Figure 1B:
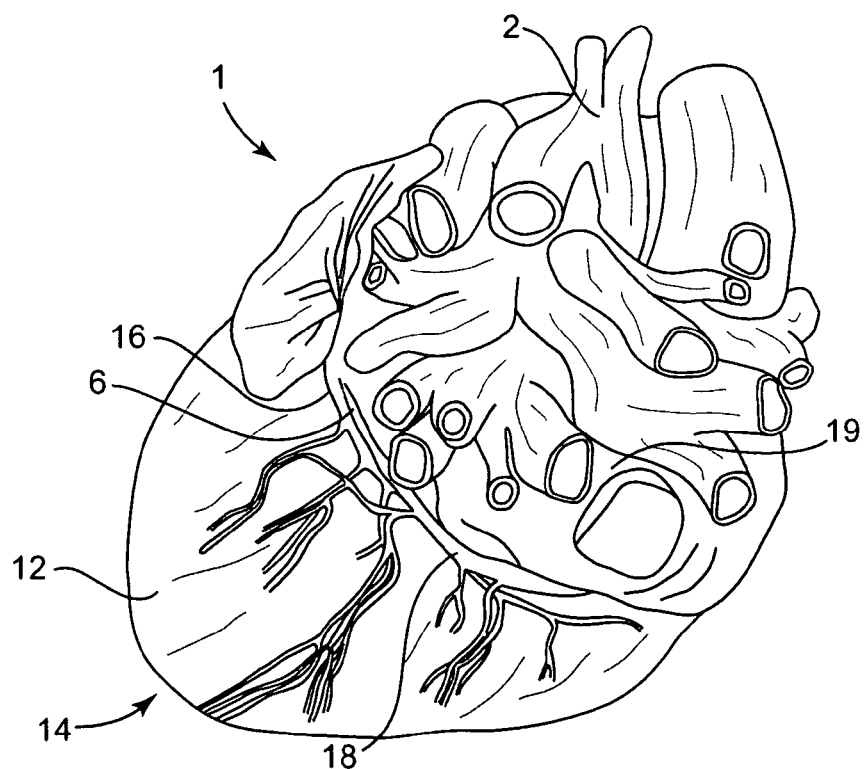
FIG. 1B is a posterior view of the heart.

FIG. 1A shows some of the arteries and veins on the left ventricle anterior and antero-lateral walls of a heart 1, and FIG. 1B shows some of the arteries and veins on the on the left ventricle posterior and postero-lateral walls of the heart 1. The aortic arch 2, left ventricle 12, and apex 14 are visible in both figures. Further visible in FIG. 1A are the left atrium 4 and the right ventricle 10. FIG. 1 also shows the left coronary artery 8 and the great coronary vein 6, which generally course side-by-side. Further visible in FIG. 1B is the right atrium 19. FIG. 1B also shows the circumflex branch of the left coronary artery 16, which generally courses side-by-side with the great coronary vein 6 and the coronary sinus 18.

Occluding agent is placed in the venous system of the heart in multiple locations so as to form a rigid or semi-rigid structure or scaffold within various segments of the cardiac venous system. The resulting structure, which may have multiple discrete parts, provides bulk to the myocardium and reinforces the myocardium in a pattern for the purpose of preventing, moderating, stopping or reversing negative cardiac remodeling due to various adverse cardiac conditions, both acute and chronic, or for the purpose of treating localize anomalies of the heart, or for both purposes. A suitable material is one that may be introduced preferably as an injectable agent in a low viscosity state into one or more sections of the venous system by preferably a minimally invasive technique, and that sets up into one or more rigid or semi-rigid masses within the venous system to support the wall of the heart where desired.

While occluding agent may be implantable, an occluding agent that is injectable and that forms a scaffold within the venous system has particular advantages. Such a scaffolding agent may be injected into the cardiac venous system so that it disperses within selected sections of the venous system under the pressure of the injection. In some cases, the scaffolding agent displaces blood as it enters into the veins. If the scaffolding agent is a polymer that crosslinks in situ as a function of time, the agent's viscosity and cure time are selected so that the material disperses to the desired extent in the veins and venules and possibly even the capillaries before it cures. A more viscous material should have a longer cure time and higher injection pressure to sufficiently disperse, while a less viscous material should have a shorter cure time so that it does not excessively disperse. Other types of scaffolding agent may crosslink under the influence of an external trigger such as light activation, or be selected to crosslink under physiologic conditions such as after exposure to body temperature, chemical exposure to physiologic chemicals (e.g., Ca, Na, etc.), and so forth. If the scaffolding agent does not crosslink in situ, its viscosity is selected so that the material disperses only to the desired extent in the veins and venules and possibly even the capillaries. An example would be a compliance gel that is a little stiffer than the collagen matrix normally present within the interstitium. Moreover, the material may be chosen such that its viscosity/elasticity is affected by pressure (viscoelastic). In this way, the material will flow in contraction but not in relaxation. Moreover, an expandable polymer may be used to create elongated structures aligned with the cardiac muscle fibers, or to enable the use of a smaller volume of injectate to minimize trauma.

A scaffolding agent containing particulates is also suitable. A particulate scaffolding agent may be injected into selected segments of the cardiac venous system, where it spreads through limited portions of the veins, venules and possibly the capillaries. The extent of penetration of the particulate scaffolding agent into a selected segment of the cardiac venous system depends on a variety of factors, including the viscosity of the injectate, the volume and pressure of the injection, the diameter of the veins, venules and capillaries, and the particulate size in the particulate scaffolding agent. A suitable particulate size for deep penetration is on the order of from about five microns to ten microns, while a suitable particulate size for shallow penetration is on the order of from about fifteen microns to thirty microns. The extent of penetration of the particulate scaffolding agent may be further controlled based on characteristics of the suspending fluid used for delivery. Suspension of the particles in a low viscosity delivery fluid, for example, would work to enhance dispersion as the fluid flows within the venous system. Inversely, a high viscosity delivery fluid would slow dispersion. In this way dispersion area may be controlled by particulate size, material properties, and suspending fluid. Moreover, a delivery fluid may be chosen that hardens (cures) over time or after exposure to external conditions (light, temperature, chemicals). The delivery fluid may be viscoelastic so that it flows in contraction but not in relaxation, or may be expandable within the veins and venules and possibly even the capillaries as it cures. As the particulate scaffolding agent enters into the veins and capillaries, it may displace the blood within the capillaries and stiffens the myocardium.

The occluding agent may be drug-eluting, so that active material may diffuse out of selected parts of the cardiac venous system continually over a period of time and penetrate into the myocardium in a release that is controlled both as to dose and regional extent. One technique for controllably releasing the active material is to contain the active material within a carrier such as a polymer scaffold or alginate or chitosan beads, which release the active material as the carrier is naturally broken down by the body over time.

Although the occluding agent occludes parts of the cardiac venous system, the occlusion is not adverse to treatment. Veins have much thinner walls with less smooth muscle than arteries do, and relative to arteries have very little elasticity because venous connective tissue contains considerably more collagen fibers than elastin fibers. Moreover, venous smooth muscle has little inherent myogenic tone. Accordingly, veins are highly distensible and have little elastic recoil, so that unblocked veins in proximity to blocked veins can easily distend to accommodate additional volumes of blood from the occluded vein with only a small increase in venous pressure.

While the occluding agent may reside as one continuous mass throughout an extended part of the cardiac venous system, greater treatment flexibility and treatment options may be realized when the occluding agent resides as multiple discrete masses within various segments of the cardiac venous system. Where global treatment is desired, the occluding agent sites conform to a pattern about one or more chambers of the heart that is suitable for reducing wall stress and stabilizing or even reducing chamber size. Some patterns also cause a beneficial global reshaping of the chamber. These changes occur quickly and are sustainable, and have a rapid and sustainable therapeutic effect on cardiac function. Over time the relief of wall stress reduces oxygen consumption and promotes healing. Moreover, various long-term therapeutic effects may be realized depending on the properties of the occluding agent, including combinations with other therapeutic materials. Specific cardiac conditions treatable by these systems and methods include, for example, dilated cardiomyopathy (with or without overt aneurismal formations), congestive heart failure, myocardial infarctions, and ventricular arrhythmias.

Figure 2:
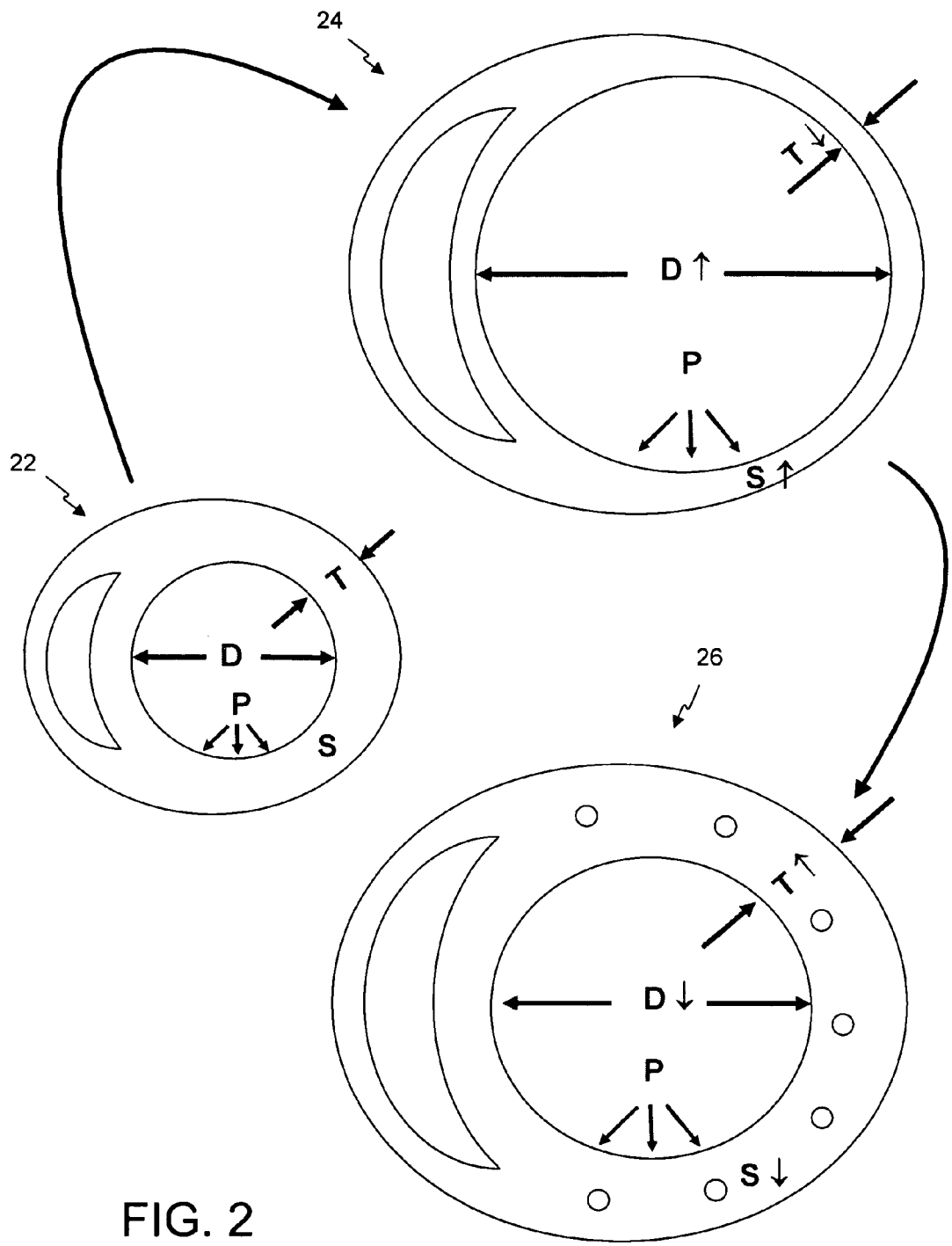
FIG. 2 is a schematic illustration of the mechanism of action for resizing a heart in heart failure, illustratively for the left ventricle.

FIG. 2 schematically illustrates the mechanism of action in a simplified manner, illustratively for the left ventricle. Wall stress "S" is an indicator of how hard the heart has to work to pump blood. Governed by the law of Laplace, wall stress is directed related to the diameter and wall thickness by the expression:

$$S=(D/T)P \quad (1)$$

where "D" is the chamber diameter, "T" is the thickness of the chamber wall, and "P" is pressure within the chamber. The heart in normal condition (reference number 22) has a left ventricle that is generally of an elongated conical shape (not shown in the plane of the drawing), which is an efficient shape for pumping. However, in heart failure patients the heart generally deteriorates to a condition (reference number 24) in which the diameter of the left ventricle gets bigger and the wall gets thinner. To achieve the same pressure P, the wall stress "S" goes up, meaning that the heart works harder. Moreover, the shape of the left ventricle (not shown in the plane of the drawing) changes from conical to spherical, which is not a efficient shape for pumping. Unfortunately, increased wall stress leads to a cascade of events which cause progressive remodeling. Remodeling stimuli resulting from increased wall stress includes cytokines, neurohormones, and oxidative stress. These remodeling stimuli cause ventricular enlargement due to myocyte hypertrophy and altered interstitial matrix, and systolic and diastolic dysfunction due to fetal gene expression, altered calcium-handling proteins, and myocyte death.

When structural material is distributed in the venous system of the heart in a suitable pattern globally about one or more chambers of the heart, here the left ventricle, the heart globally improves to a condition (reference number 26) in which the wall of the left ventricle thickens and the chamber diameter decreases. As thickness goes up and diameter goes down, the wall stress "S" is reduced. The cascade of events that result in progressive remodeling is interrupted, and progressive remodeling is halted or even reversed.

Figure 3:
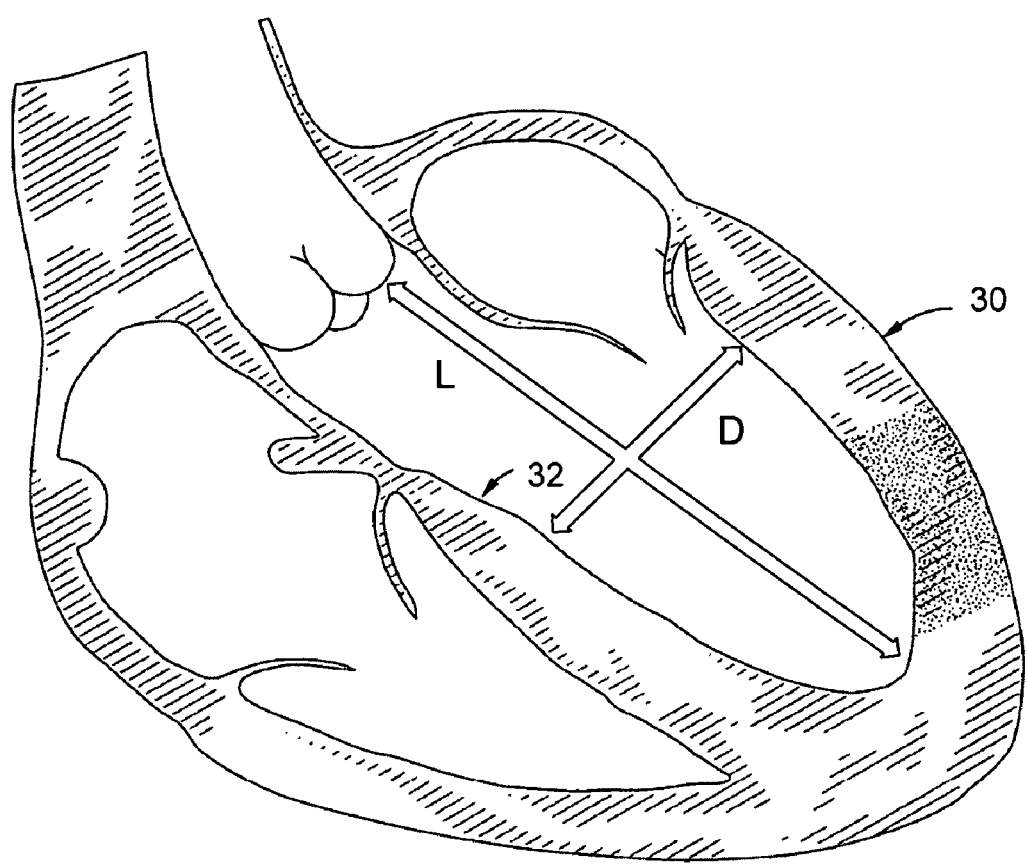
FIG. 3 is a cross-section drawing of a heart in which the long axis and short axis of the left ventricle are identified.

Some patterns also cause a beneficial reshaping of the chamber, effectively reversing LV remodeling for the treatment of heart failure. The shape of the left ventricle may be roughly quantified using, for example, the "end-systolic sphericity index," which as shown in FIG. 3 for the left ventricle 32 of heart 30, is the ratio of the long axis length "L" to the mid-cavity diameter "D," both measured at end systole. The normal cardiac sphericity index decreases as the shape of the left ventricle deviates from the ideal conical shape and approaches spherical. Reshaping to a more physiological ellipsoid shape, and in particular to a conical shape, is desirable.

Figure 4:
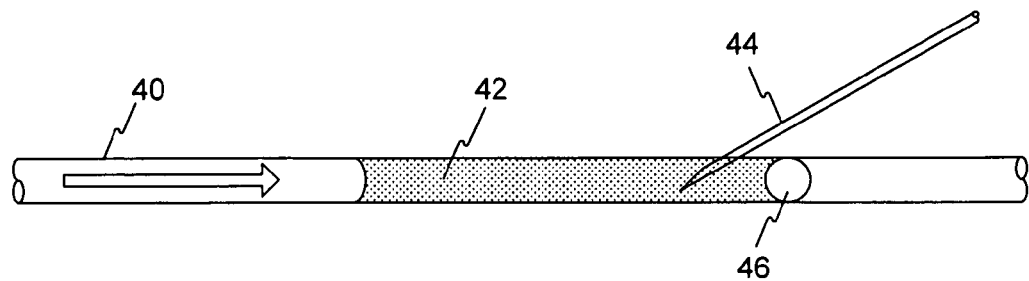
FIG. 4 is a sectional view of a retrograde injection through a vein wall into a venous system segment having a downstream occluder in place.
Figure 5:
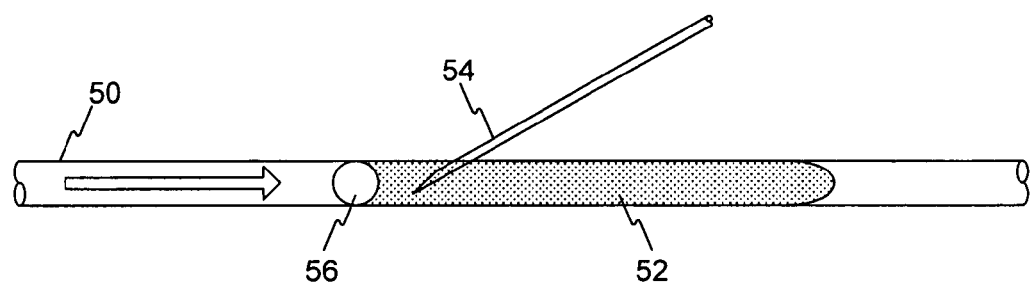
FIG. 5 is a sectional view of a retrograde injection through a vein wall into a venous system segment having an upstream occluder in place.
Figure 6:
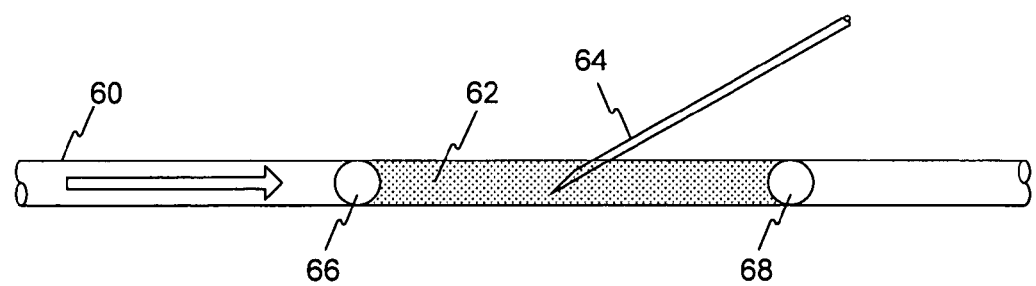
FIG. 6 is a sectional view of an injection through a vein wall into a venous system segment defined by two occluders in place.
Figure 7:
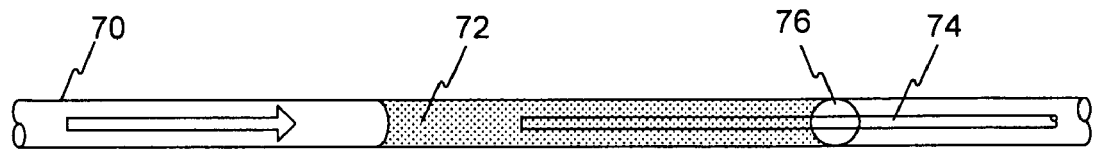
FIG. 7 is a sectional view of a retrograde injection from within the vein into a venous system segment having a downstream occluder in place.
Figure 8:
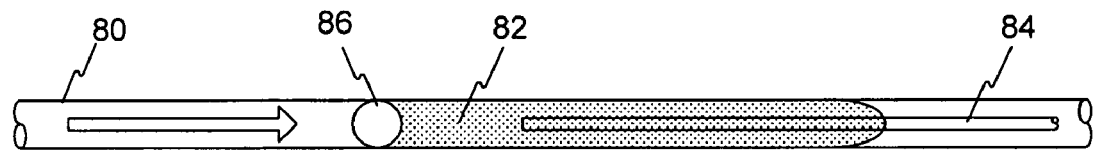
FIG. 8 is a sectional view of a retrograde injection from within the vein into a venous system segment having an upstream occluder in place.
Figure 9:
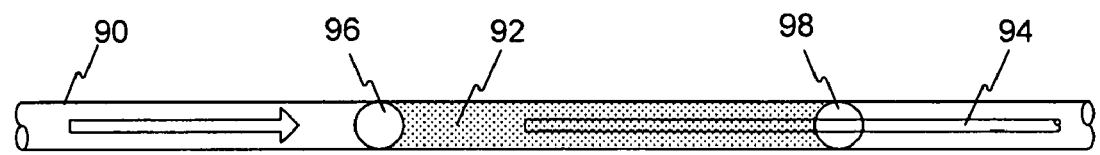
FIG. 9 is a sectional view of an injection from within the vein into a venous system segment defined by two occluders in place.

Patterns suitable for global resizing may also be used as is or augmented by supplemental patterns to treat localized conditions, such as myocardial infarctions and overt aneurysm of the ventricular wall (as typically forms in response to large transmural myocardial infarctions). These techniques may also be used to treat localized conditions that may not yet have progressed to cardiomyopathy.

Where the occluding agent is injectable, a suitable injection technique may be used so that the occluding agent in combination with the use of one or more occluding barriers does not escape into the capillary system or become entrained in the venous return and flow into the heart. As shown in FIGS. 4-9 in simplified form for ease of explanation, a suitable occluder such as a balloon, suture, clamp, fast setting surgical adhesive, or another biocompatible polymer material may be used in the vein near the injection site to block the venous flow so that the occluding agent may flow into the desired section of the cardiac venous system and cure. The injection into the vein may be retrograde, and may be made through the wall of the vein, or from within the vein and through an occluder, or from within the vein and downstream of an occluder, or from within the vein and through an occluder into a space between two occluders. FIG. 4 shows injection of occluding agent 42 through a needle 44 into a vein 40 upstream of an occluder 46. FIG. 5 shows injection of occluding agent 52 through a needle 54 into a vein 50 downstream of an occluder 56. FIG. 6 shows injection of occluding agent 62 through a needle 64 into a vein 60 between an occluder 66 and an occluder 68. FIG. 7 shows injection of occluding agent 72 through a catheter 74 that passes through an occluder 76 within a vein 70. FIG. 8 shows injection of occluding agent 82 through a catheter 84 within a vein 80 and downstream of an occluder 86. FIG. 9 shows injection of occluding agent 92 into a space between two occluders 96 and 98 within a vein 90 via a catheter 94 that passes through the occluder 98.

While not shown in the simplified schematic representations of FIGS. 4-9, the occluding agent spreads within some localized region into the wall of the heart via branches in the cardiac venous system, since the venous system network of the heart is distributed throughout the thickness of the heart muscle. This dispersal advantageously enhances the thickening and strengthening effect of the occluding agent.

While the use of one or more occluders may be desirable under many circumstances, the use of an occluder is not necessary. Occluders may not be necessary if the vein is already occluded, or if the injectable occluding agent is a very rapidly setting material.

While some conditions may be treated in one procedure, other conditions may preferably be treated in multiple procedures over time. Various localized regions may be treated successively over time. One localized region may be treated, and the effect studied before deciding the treatment to be applied to other localized regions. The treatments may be applied to fine tune the beneficial results. The various material properties of the occluding agent such as stiffness, compliance, and resorption rate may be tailored to be matched to the particular treatment.

Identifying the sections of the cardiac venous system into which a suitable occlusion agent may be placed may be done empirically. Alternatively, computer-aided selection may be practiced if desired. In one suitable technique, finite element model simulation is used to model a region of the heart such as the left ventricle. Using any suitable imaging or mapping technique, parameters of the patient's left ventricle, including the location, extent and thickness of damaged wall areas, are measured and added to the model. Injection of material into selected segments of the venous system may be simulated by changing the transmural coordinates of epicardial and endocardial mesh nodes in border zone elements corresponding to the selected segments, along with changing the contractility of the elements. The selected segments may be changed over successive simulations to identify an optimal set of venous system segments to receive injections. A suitable finite element model simulation is disclosed in an article by Samuel T. Wall et al., Theoretical Impact of the Injection of Material Into the Myocardium: A Finite Element Model Simulation, in Circulation AHA 106.657270, Nov. 27, 2006, which is incorporated herein in its entirety by reference thereto.

Patterns of Distribution of Occluding Agent Sites

Various segments of the cardiac venous system may be selected as occluding agent sites for forming a therapeutically effective pattern for the local treatment of heart anomalies, or for the global treatment of individual chambers of the heart such as a ventricle or an atrium, or for the global treatment of multiple chambers of the heart, or of the entire heart. Where a global treatment is desired, mapping need not be performed. A global approach is particularly applicable to the ventricles and especially the left ventricle, but may also be used reshape and/or resize the atria, and in particular an enlarged left atrium, to aid in prevention of atrial fibrillation and other atria-related conditions. Where a local treatment is desired, the location of a heart disorder such as a myocardial infract or aneurysmal thinning may be identified, and segments of the cardiac venous system conforming to a therapeutically effective pattern of occluding agent sites for treating the localized heart disorder may be determined. Suitable techniques for identifying various heart disorders such as thin walled regions or aneurysms requiring treatment may be identified by MRI, echo, electrical, and other imaging and mapping modalities. Patterning for treatment of a localized heart anomaly may be done on its own or as part of a global treatment. Where used along with a global treatment, the local pattern may be envisioned separate from the global pattern, or integrated into the global pattern.

For treatment, occluding agent is placed in discrete masses within various segments of the venous system, where the distribution of the segments generally conform to a therapeutically effective local pattern proximate a localized heart anomaly, or where the segments generally conform to a therapeutically effective global pattern entirely or partially about one or more chambers of the heart. The patterns may be envisioned as shaped distributions of occluding agent sites, or even more simply as one or more lines (including band, arc, curve both regular and irregular, and so forth) of occluding agent sites. The pattern may be envisioned relative to the entire heart, to one or more ventricles of the heart, to one or more atria of the heart, or to striations of the myocardial tissue to effect a global resizing and/or reshaping of the heart or one or more of its various chambers. In one suitable type of pattern, one or more lines may be envisioned that extend circumferentially about whole or part of one or more heart chambers such as the atria and ventricles. In the case of the left ventricle, for example, one or more such circumferential lines may be used, depending on the degree of enlargement of the left ventricle and the type of reshaping desired. The number of occluding agent sites per circumferential line depends on the size of the heart and location of the line, but may involve from, illustratively, three to nine occluding agent sites, or preferably from six to seven occluding agent sites (three or four on the anterior and lateral surfaces, and three on the posterior surface) in a typical mammalian heart if the veins available for injection are used. In another suitable pattern, lines may be envisioned that extend longitudinally the whole distance or part of the distance from proximate the apex to proximate the base. In the case of the left ventricle, for example, two or more such longitudinal lines may be used, depending on the degree of enlargement of the left ventricle and the type of reshaping desired. The number of occluding agent sites per longitudinal line depends on the size of the heart and location of the line, but may involve from, illustratively, three to seven occluding agent sites, or preferably from four to six occluding agent sites. Where injections are used to form the discrete masses, the injections may be but need not necessarily be of uniform dose and type of occluding agent, and the vein sections into which the injectate is introduced may lie upon or within the myocardium. Where implants are used, the implants may be, but need not necessarily be, of the same size and type of material, and the vein sections into which the implants are introduced may lie upon or within the myocardium.

FIGS. 10-14 show one type of suitable pattern, envisioned as one or more lines that extend circumferentially about the left ventricle. FIGS. 15-16 show another type of suitable pattern, envisioned as multiple lines that extend longitudinally the whole distance from proximate the apex to proximate the base along the left ventricle or both the left and right ventricles. FIG. 17 shows that patterns of both types may be used. FIGS. 18-21 show various local patterns that may be used to treat localized anomalies of the heart.

Figure 10A:
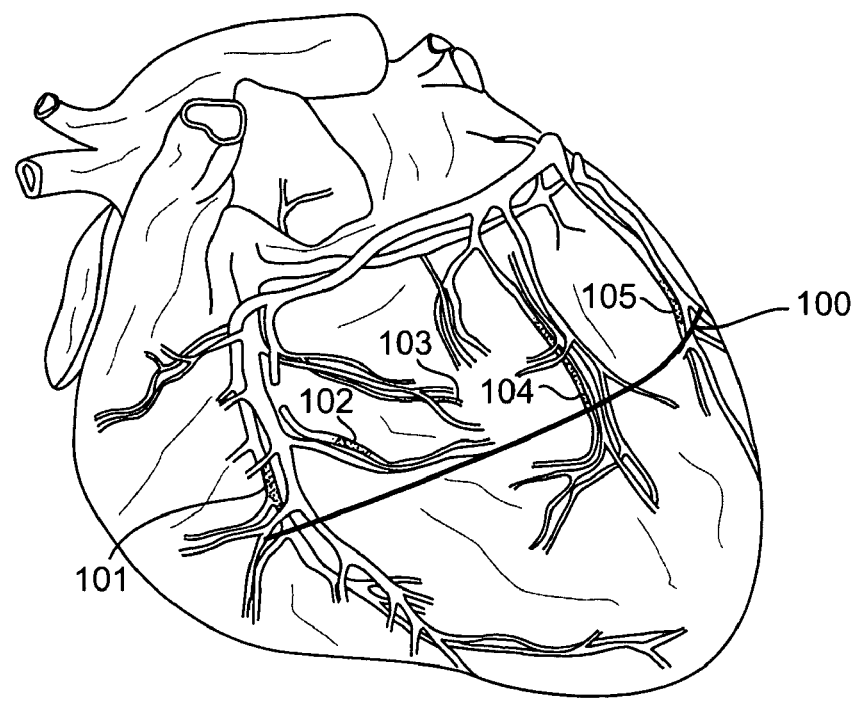
FIG. 10A is an anterior plan view of a heart in which occluding agent sites within the cardiac venous system generally conform to a pattern of one circumferential line.
Figure 10B:
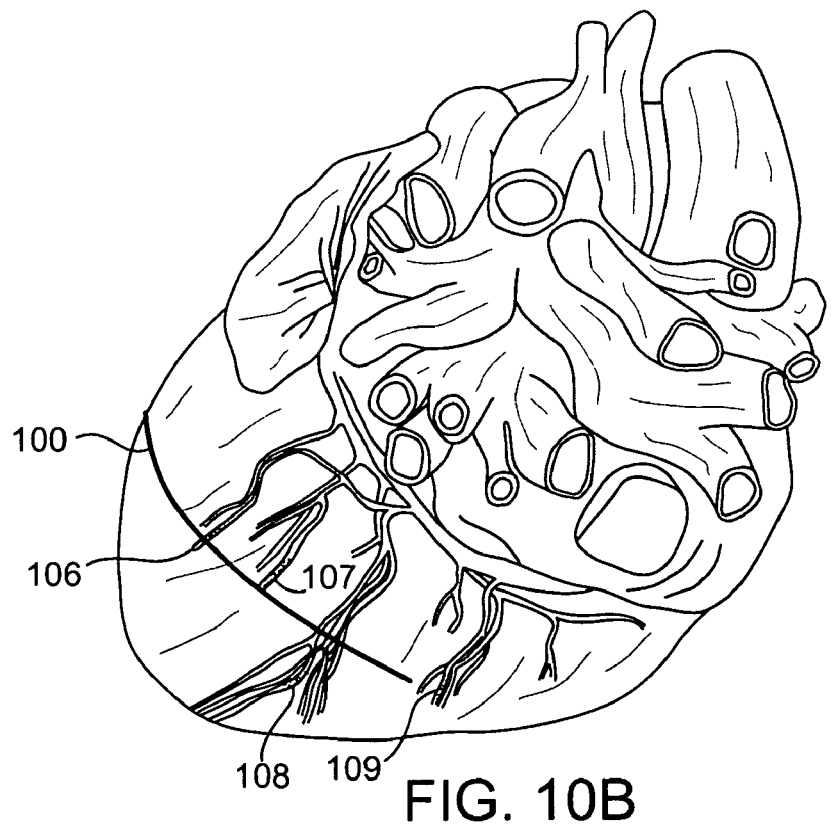
FIG. 10B is a posterior plan view of the heart of FIG. 10A.

FIG. 10A is an anterior plan view and FIG. 10B is a posterior view of a heart in which the distribution of occluding agent sites, which are represented as speckled segments 101-109 within specific vein segments of the cardiac venous system, may be envisioned as generally conforming to a line 100 which circumferentially spans across most of the left ventricle free wall at the near widest part of the ventricle. In this image, the free wall runs from anterior and anterior lateral and around the back of this view to the posterior lateral surface of the heart. The line 100 is shown as being slightly spaced away from the occluding agent sites so that the sites 101-109 can be better identified on the heart.

Figure 11A:
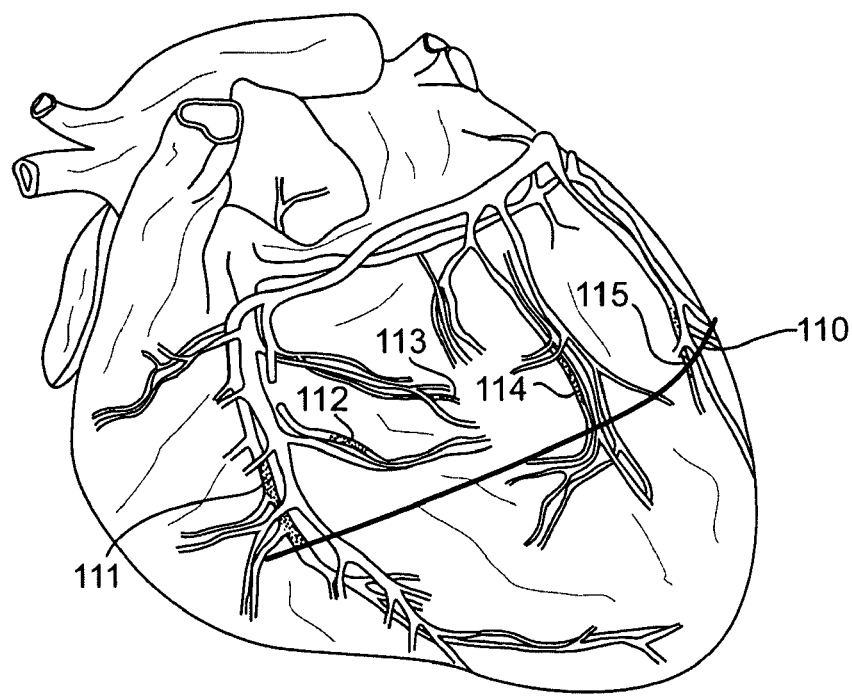
FIG. 11A is an anterior plan view of a heart in which occluding agent sites within the cardiac venous system generally conform to a pattern of one circumferential line.
Figure 11B:
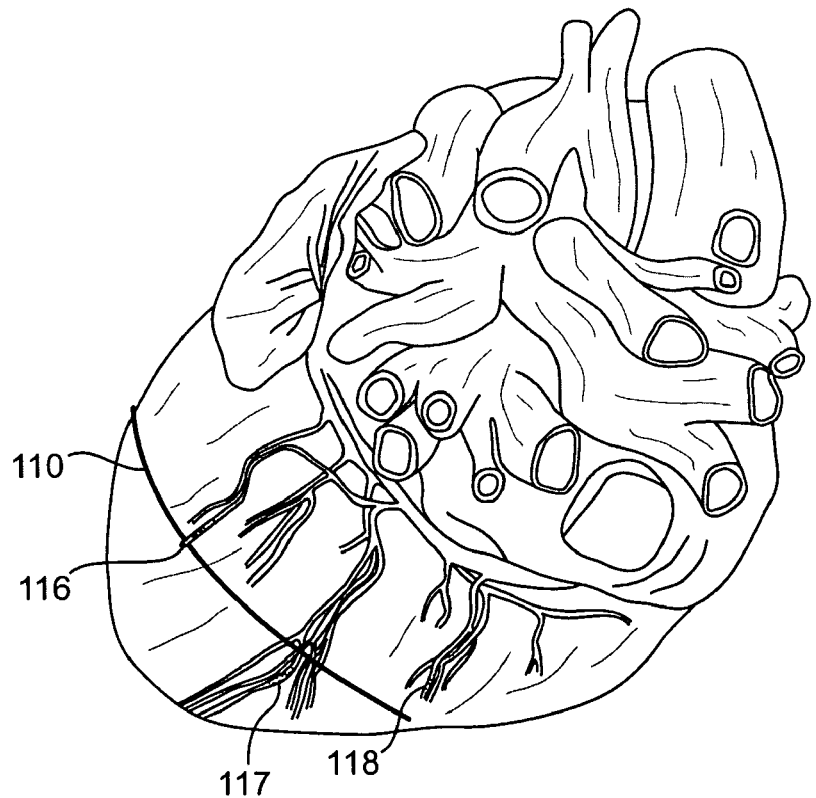
FIG. 11B is a posterior plan view of the heart of FIG. 11A.

The location of the pattern may be adjusted by shifting the positions of the occluding agent sites. FIG. 11A is an anterior plan view and FIG. 11B is a posterior view of a heart in which the distribution of the occluding agent sites 111-119 is slightly different than the distribution of the occluding agent sites 101-109 (FIGS. 10A and 10B). As a result, the pattern may be envisioned as a line 110 which circumferentially spans across most of the left ventricle free wall at the near widest part of the ventricle, but at a slightly different location than the line 100 (FIGS. 10A and 10B). The different locations of the lines 100 and 110 in FIGS. 10 and 11 may differently impact the reshaping achieved by the respective patterns. The line 110 is shown as being slightly spaced away from the occluding agent sites so that the sites 111-119 can be better identified on the heart.

Figure 12A:
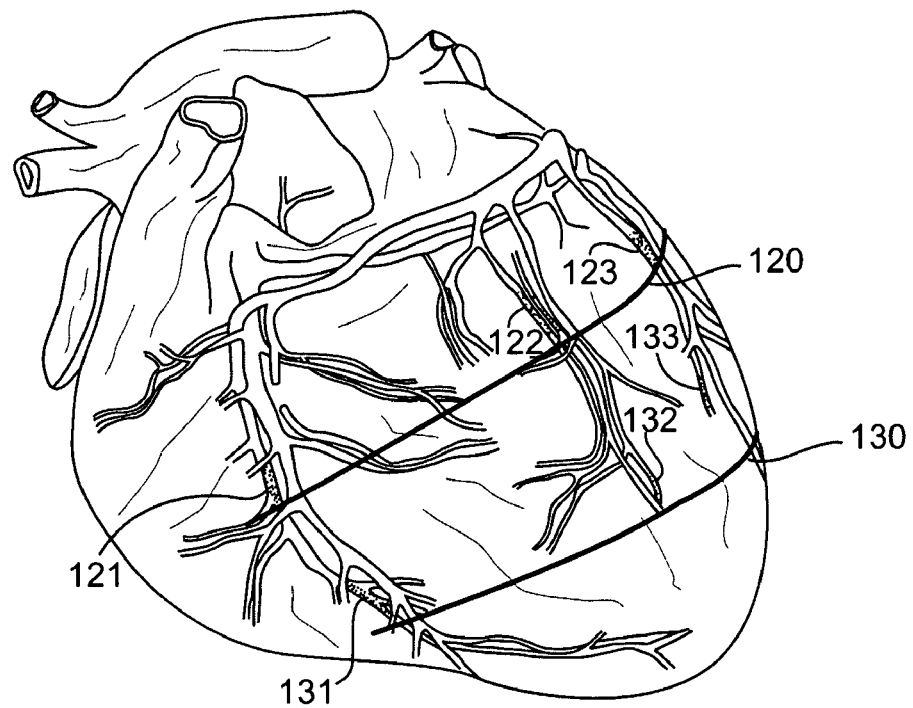
FIG. 12A is an anterior plan view of a heart in which occluding agent sites within the cardiac venous system generally conform to a pattern of two circumferential lines.
Figure 12B:
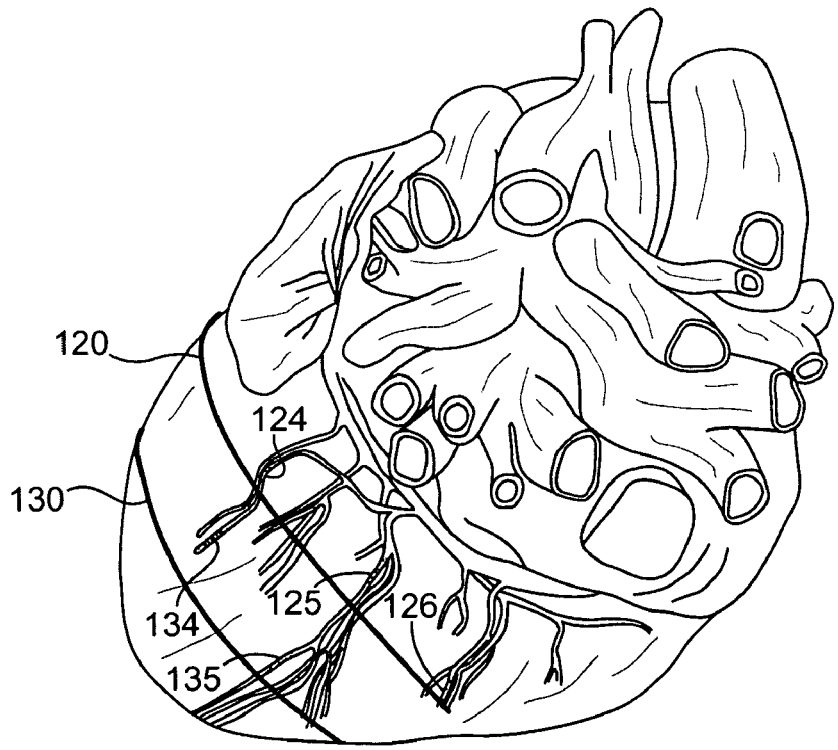
FIG. 12B is a posterior plan view of the heart of FIG. 12A.

FIG. 12A is an anterior plan view and FIG. 12B is a posterior view of a heart in which the distribution of occluding agent sites may be envisioned as generally conforming to a pattern of two lines 120 and 130 which circumferentially span across most of the left ventricle free wall in proximity to the near widest part of the ventricle. The distribution of occluding agent sites 121-126 may be envisioned as generally conforming to the line 120, while the distribution of occluding agent sites 131-135 may be envisioned as generally conforming to the line 130. In this image, the free wall runs from anterior and anterior lateral and around the back of this view to the posterior lateral surface of the heart. The lines 120 and 130 are shown as being slightly spaced away from the occluding agent sites 121-126 and 131-135 so that these sites can be better identified on the heart.

Figure 13A:
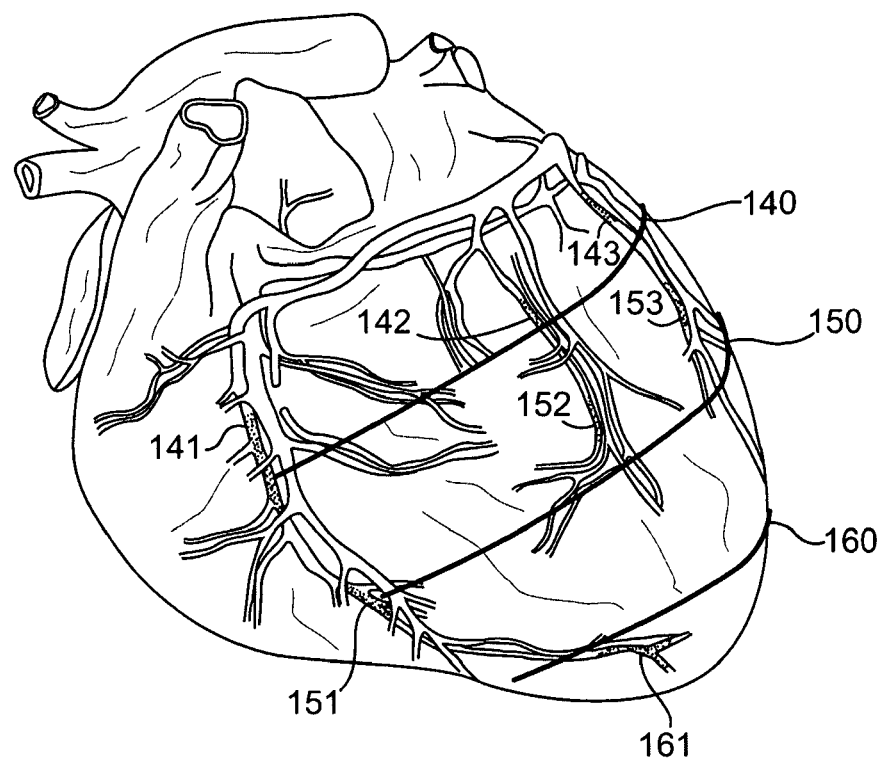
FIG. 13A is an anterior plan view of a heart in which occluding agent sites within the cardiac venous system generally conform to a pattern of three circumferential lines.
Figure 13B:
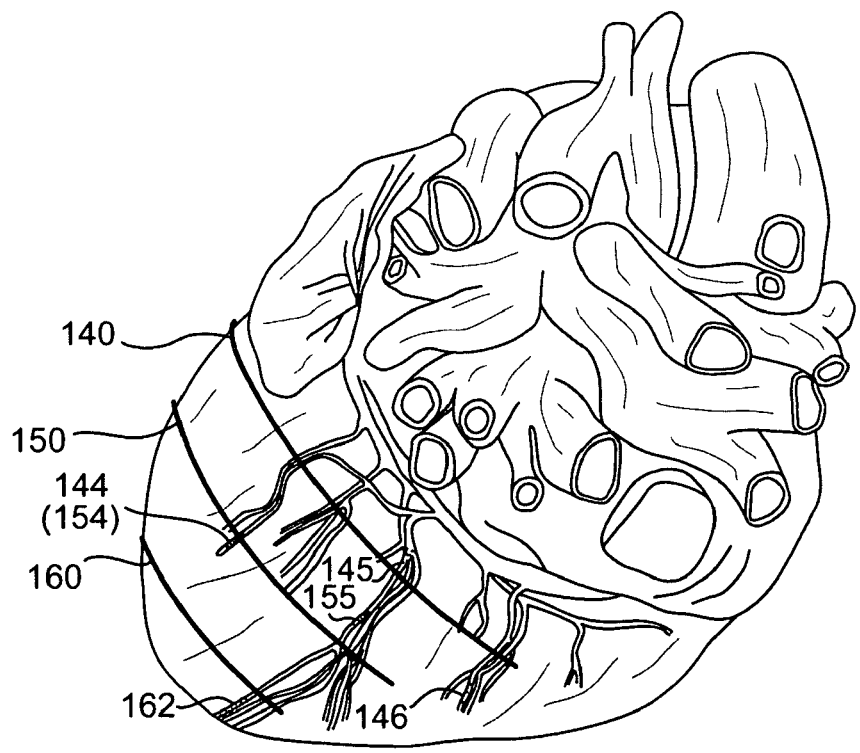
FIG. 13B is a posterior plan view of the heart of FIG. 13A.

FIG. 13A is an anterior plan view and FIG. 13B is a posterior view of a heart in which the distribution of occluding agent sites may be envisioned as generally conforming to a pattern of three lines 140, 150 and 160 which circumferentially span across most of the left ventricle free wall. Line 140 illustratively is in proximity to the near widest part of the ventricle, while lines 150 and 160 are spaced away toward the apex. Alternatively, lines 140 and 150 may both be in proximity to the near widest part of the ventricle, while line 160 may be spaced away toward the apex. The distribution of occluding agent sites 141-146 may be envisioned as generally conforming to the line 140, the distribution of occluding agent sites 151-155 may be envisioned as generally conforming to the line 150, and the distribution of occluding agent sites 161-162 may be envisioned as generally conforming to the line 160. The occluding agent site 144 is also identified by the reference numeral 154 to indicate that it may be envisioned as generally conforming to both the lines 140 and 150. In this image, the free wall runs from anterior and anterior lateral and around the back of this view to the posterior lateral surface of the heart. The lines 140, 150 and 160 are shown as being slightly spaced away from the occluding agent sites 141-146, 151-155, and 161-162 so that these sites can be better identified on the heart.

Figure 14A:
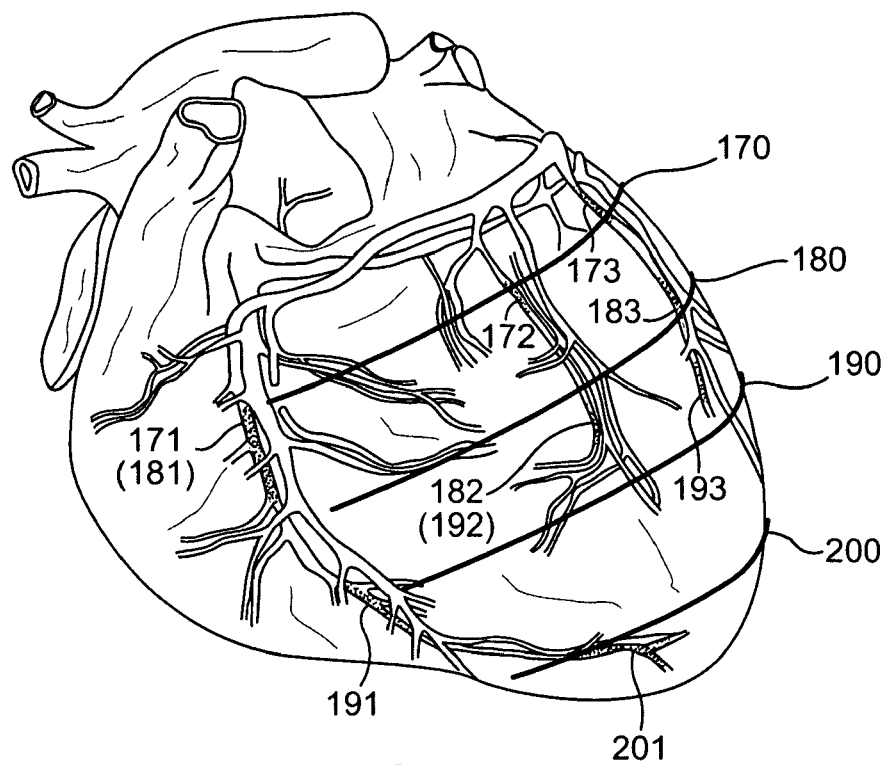
FIG. 14A is an anterior plan view of a heart in which occluding agent sites within the cardiac venous system generally conform to a pattern of four circumferential lines.
Figure 14B:
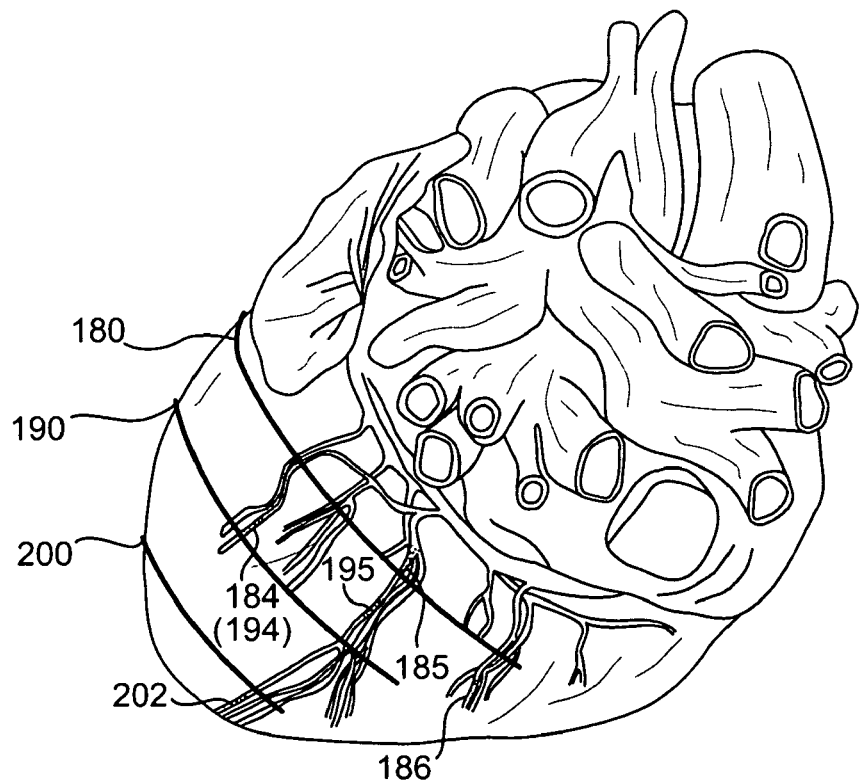
FIG. 14B is a posterior plan view of the heart of FIG. 14A.

FIG. 14A is an anterior plan view and FIG. 14B is a posterior view of a heart in which the occluding agent sites may be envisioned as defining a pattern of four lines 170, 180, 190 and 200 which circumferentially span across most of the left ventricle free wall. Lines 170 and 180 illustratively are in proximity to the near widest part of the ventricle, while lines 190 and 200 are spaced away toward the apex. The distribution of occluding agent sites 171-173 may be envisioned as generally conforming to the line 170, the distribution of occluding agent sites 181-186 may be envisioned as generally conforming to the line 180, the distribution of occluding agent sites 191-195 may be envisioned as generally conforming to the line 190, and the distribution of occluding agent sites 201-202 may be envisioned as generally conforming to the line 200. The occluding agent site 171 is also identified by the reference numeral 181 to indicate that it may be envisioned as generally conforming to both the lines 170 and 180. Similarly, the occluding agent sites 182 and 184 are also identified by the reference numerals 192 and 194 respectively to indicate that they may be envisioned as generally conforming to both the lines 180 and 190. In this image, the free wall runs from anterior and anterior lateral and around the back of this view to the posterior lateral surface of the heart. The lines 170, 180, 190 and 200 are shown as being slightly spaced away from the occluding agent sites 171-173, 181-186, 191-195 and 200-201 so that these sites can be better identified on the heart.

Figure 15A:
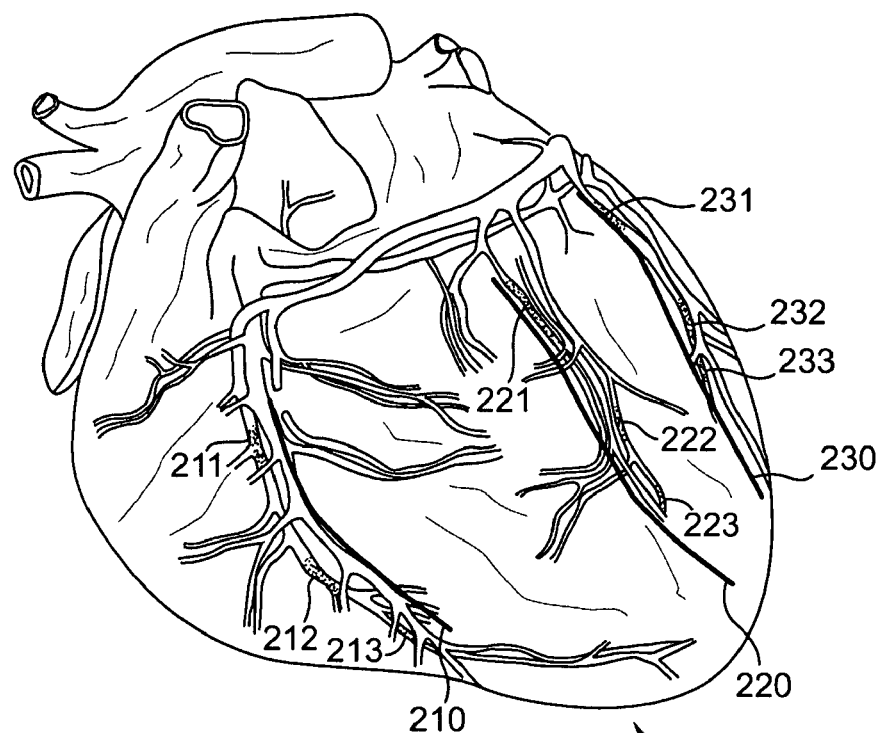
FIG. 15A is an anterior plan view of a heart in which occluding agent sites within the cardiac venous system generally conform to a pattern of six longitudinal lines.
Figure 15B:
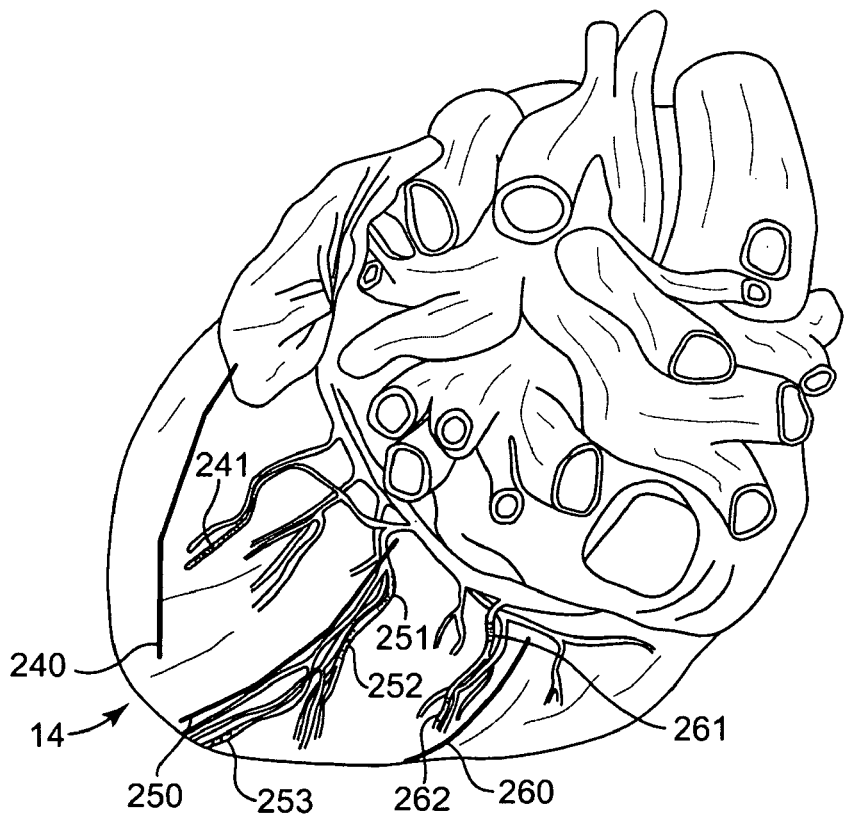
FIG. 15B is a posterior plan view of the heart of FIG. 15A.

FIG. 15A is an anterior plan view and FIG. 15B is a posterior view of a heart in which the distribution of occluding agent sites may be envisioned as generally conforming to a pattern of six lines 210, 220, 230, 240, 250 and 260 which longitudinally span along most of the left ventricle free wall. The distribution of occluding agent sites 211-213 along with the apex 14 may be envisioned as generally conforming to the line 210, the distribution of occluding agent sites 221-223 along with the apex 14 may be envisioned as generally conforming to the line 220, the distribution of occluding agent sites 231-233 along with the apex 14 may be envisioned as generally conforming to the line 230, the distribution of occluding agent site 241 along with the apex 14 may be envisioned as generally conforming to the line 240, the distribution of occluding agent sites 251-253 along with the apex 14 may be envisioned as generally conforming to the line 250, and the distribution of occluding agent sites 261-262 along with the apex 14 may be envisioned as generally conforming to the line 260. In this image, the free wall runs from anterior and anterior lateral and around the back of this view to the posterior lateral surface of the heart. The lines 210, 220, 230, 240, 250 and 260 are shown as being slightly spaced away from the occluding agent sites 211-213, 221-223, 231-233, 241, 251-253 and 261-262 so that these sites can be better identified on the heart.

While the patterns of FIGS. 10-15 are specific to the left ventricle, the techniques may be used on other chambers of the heart or even on the whole heart. The techniques may be used to reshape and/or remodel the atria, and in particular an enlarged left atrium, to aid in prevention of atrial fibrillation and other atria-related conditions.

Figure 16A:
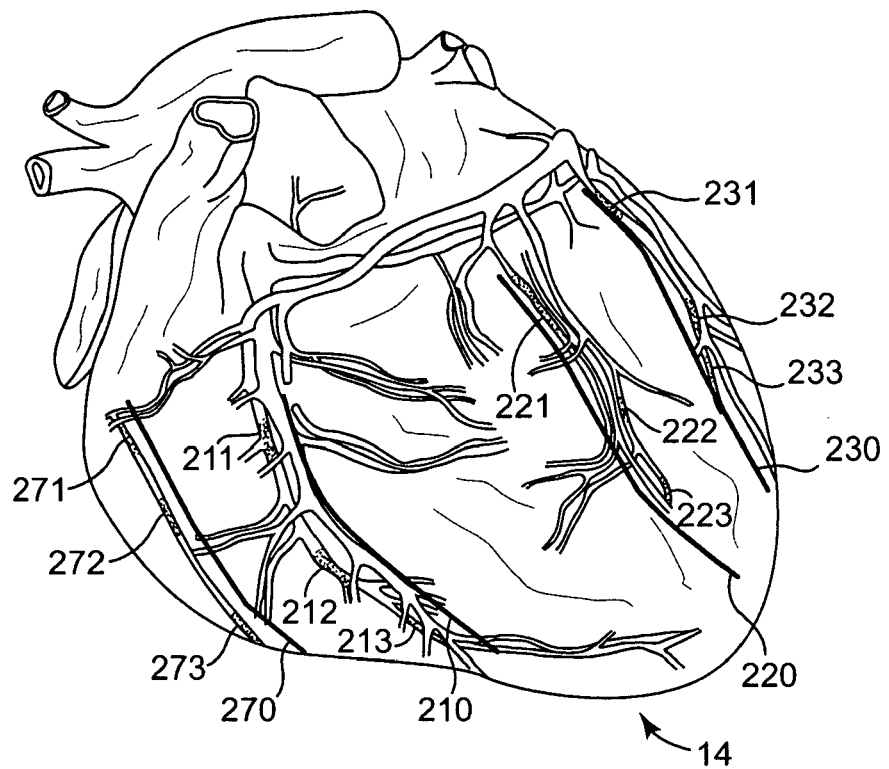
FIG. 16A is an anterior plan view of a heart in which occluding agent sites within the cardiac venous system generally conform to a pattern of seven longitudinal lines.
Figure 16B:
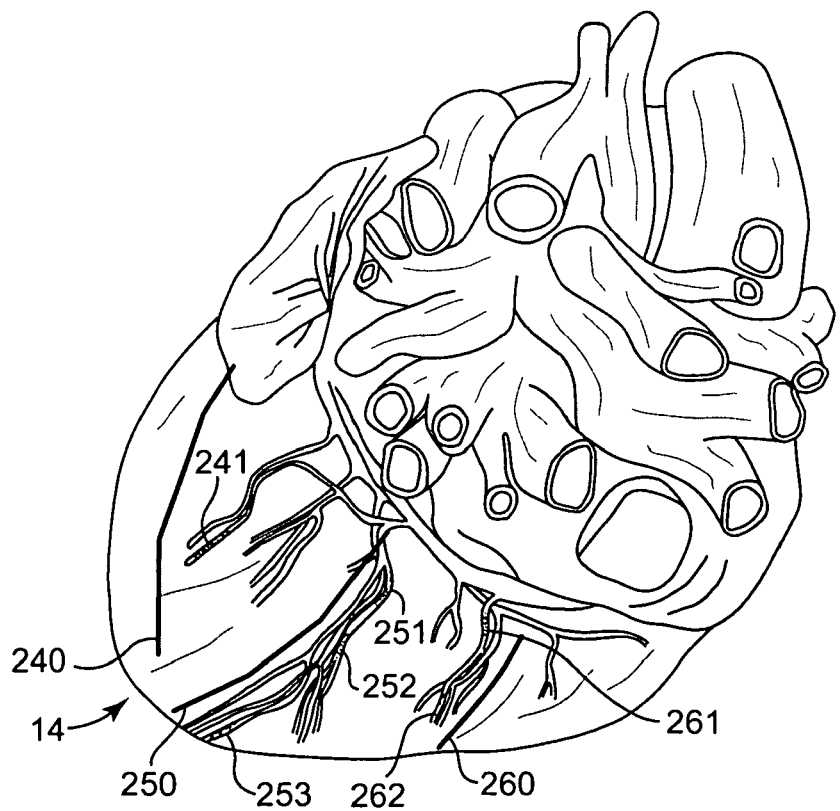
FIG. 16B is a posterior plan view of the heart of FIG. 16A.

A pattern that may be used for treating the left and right ventricles is shown in FIGS. 16A and 16B. Lines 210, 220, 230, 240, 250 and 260 are the same as the lines shown in FIGS. 15A and 15B to treat the left ventricle. In addition, a distribution of occluding agent sites 271, 272 and 273 generally conforming to longitudinal line 270 is used to treat the right ventricle.

Figure 17A:
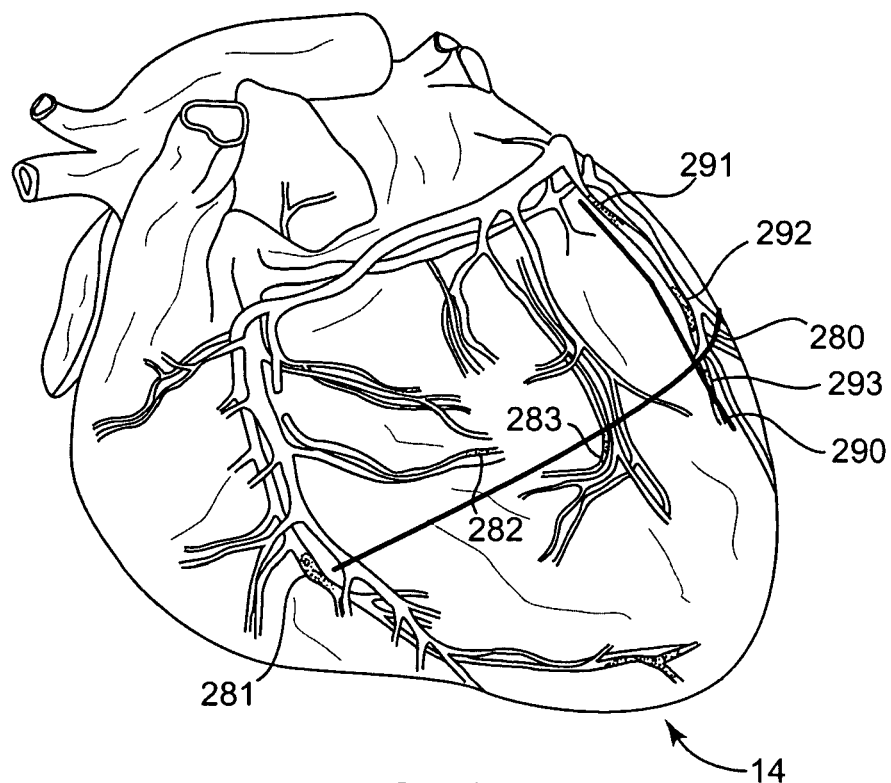
FIG. 17A is an anterior plan view of a heart in which occluding agent sites within the cardiac venous system generally conform to a pattern of one circumferential line and one longitudinal line.
Figure 17B:
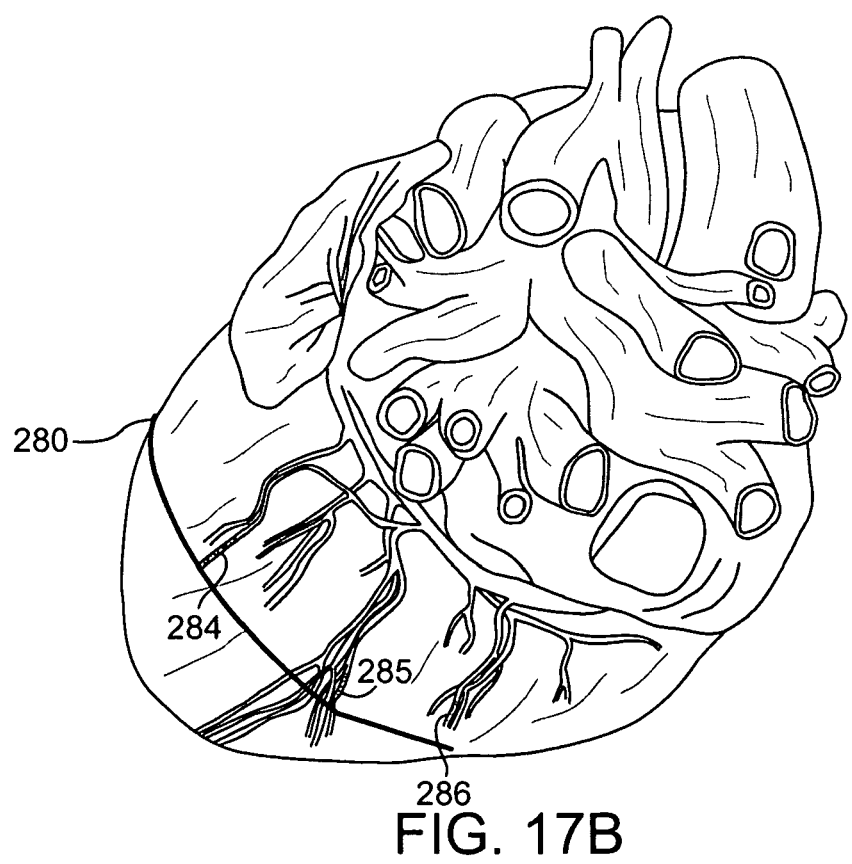
FIG. 17B is a posterior plan view of the heart of FIG. 17A.

A pattern may also include lines of different orientations. FIG. 17A is an anterior plan view and FIG. 17B is a posterior view of a heart in which the distribution of occluding agent sites 281-286 generally conform to a line 280 which circumferentially spans across most of the left ventricle free wall at the near widest part of the ventricle, and the distribution of occluding sites 291-293 and the apex 14 generally conform to a line 290 which extends longitudinally the whole distance from proximate the apex to proximate the base. In this image, the free wall runs from anterior and anterior lateral and around the back of this view to the posterior lateral surface of heart. Line 280 and 290 are shown as being slightly spaced away from the occluding agent sites 281-286 and 291-293 so that these sites can be better identified on the heart.

A pattern may also include sites outside of the cardiac venous system. In one technique for treating cardiomyopathy, space-occupying agent is introduced into sites within the myocardium, such that the space-occupying agent integrates into and thickens at least part of the cardiac wall about the heart chamber or chambers. Together with the occluding agent sites, the space-occupying agent sites form patterns that are therapeutically effective for reducing globally wall stress, stabilizing or even reduce chamber size, and causing a beneficial global reshaping of the chamber. This technique and others are described in U.S. patent application Ser. No. 11/900,005 filed Sep. 7, 2007 (Sabbah et al., Intramyocardial Patterning for Global Cardiac Resizing and Reshaping), which hereby is incorporated herein in its entirety by reference thereto. Various other techniques may also be suitable for extending or completing patterns that include occluding agent sites in the cardiac venous system.

Treatment of Localized Conditions

Figure 18:
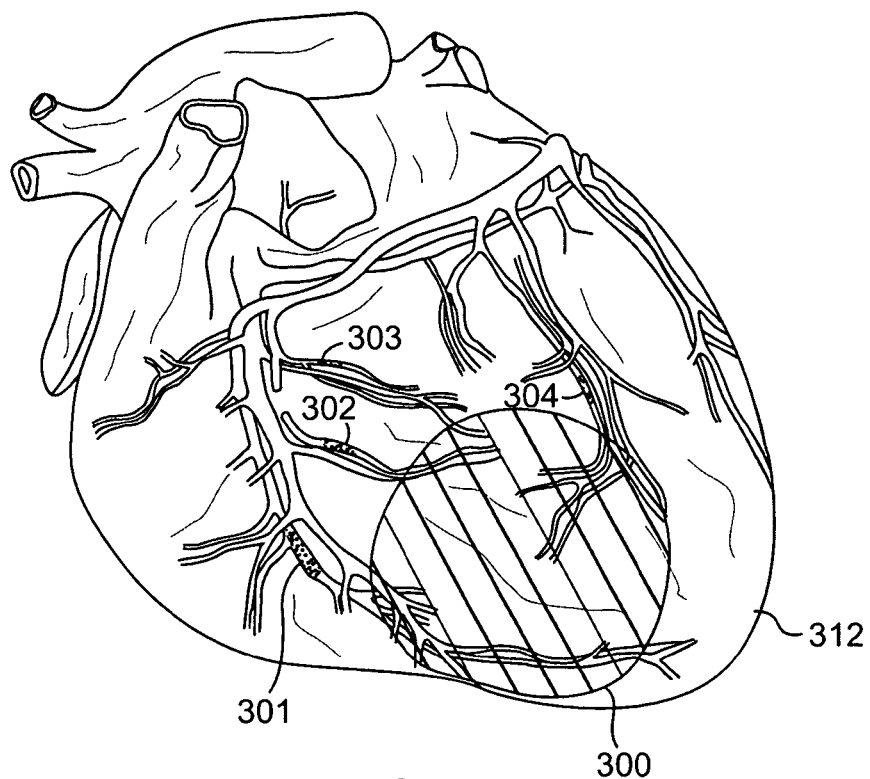
FIG. 18 is an anterior plan view of a heart in which occluding agent sites within the cardiac venous system lie in proximity to an aneurysm.
Figure 19:
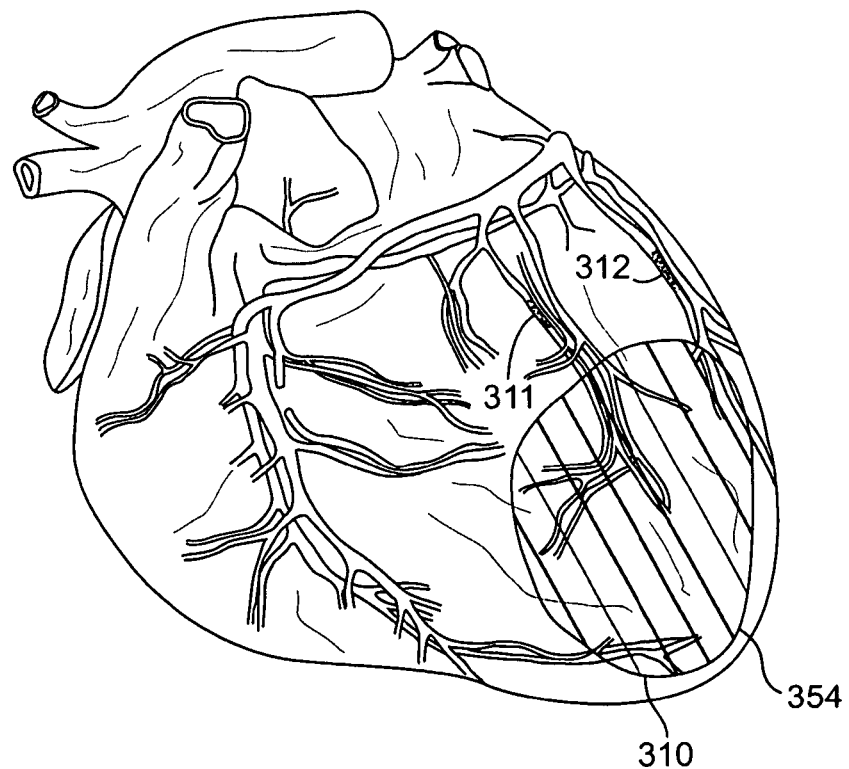
FIG. 19 is an anterior plan view of a heart in which occluding agent sites within the cardiac venous system lie in proximity to another aneurysm.

Patterns of occluding agent sites may be used to treat localized conditions such as myocardial infarctions and overt aneurysm of the ventricular wall. FIG. 18, for example, shows a pattern of occluding agent sites 301-304 arranged about the periphery of an aneurysm 300, to relieve stress in the transition area between healthy cardiac tissue and the myocardial infarct. FIG. 19 shows a pattern of occluding agent sites 311-312 arranged about the periphery of a different aneurysm 310, to relieve stress in the transition area between healthy cardiac tissue and the myocardial infarct. Suitable techniques for identifying various heart disorders such as thin walled regions or aneurysms requiring treatment are known to a person of ordinary skill in the art, and include MRI, echo, and other imaging modalities. These techniques may be used with global patterns to treat cardiomyopathy, and may be used without global patterns to treat localized conditions that may not yet have progressed to cardiomyopathy.

Figure 20:
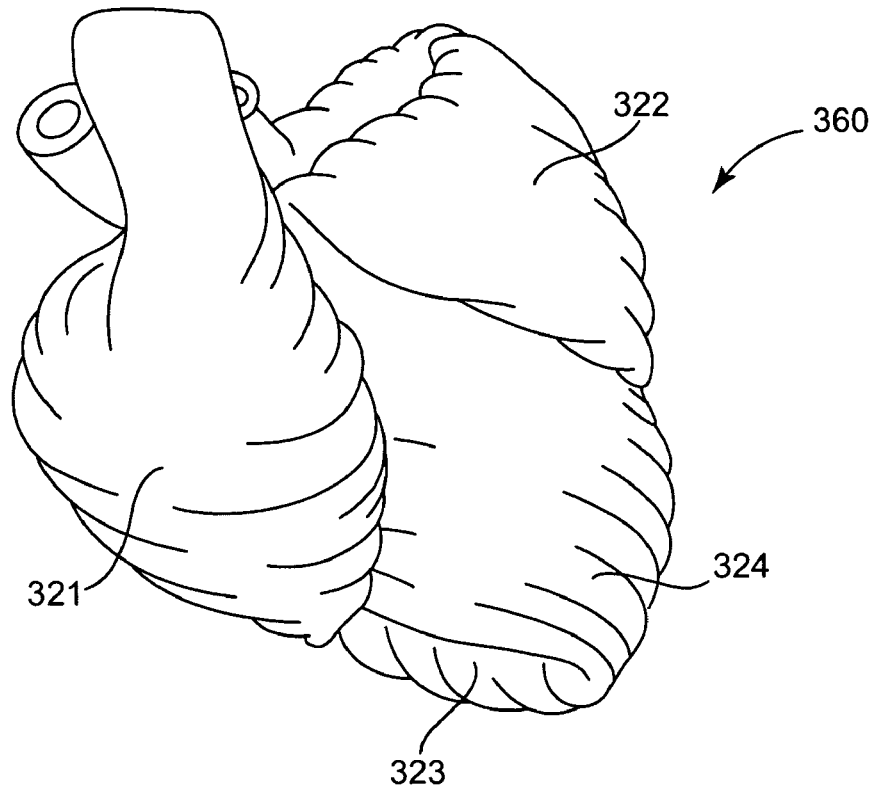
FIG. 20 is a schematic drawing of an anterior aspect of a heart in accordance with the Torrent-Guasp double loop concept.

In some treatments, it may be desirable to align the occluding agent site with the striations of the heart. FIG. 20 is a schematic drawing of an anterior aspect of a heart in accordance with the Torrent-Guasp double loop concept. The representation of FIG. 20 shows right segment 321 of the basal loop, left segment 322 of the basal loop, descending segment 323 of the apical loop, and ascending segment 324 of the apical loop. Notice that the striations in the various segments 321, 322, 323 and 324 represent muscle fiber bundles of the myocardium. The Torrent-Guasp double loop concept is disclosed in F. Torrent-Guasp et al., Towards new understanding of the heart structure and function, European Journal of Cardio-thoracic Surgery, Vol. 27, 2005, pages 191-201, which hereby is incorporated herein in its entirety by reference thereto. The striations may be used to improve treatment in the following manner.

Patterns may be envisioned relative to striations of the myocardial tissue to effect a global resizing and/or reshaping of the heart or one or more of its various chambers. Illustratively, line patterns running parallel to the striations may be used to effect a global resizing and/or reshaping.

Figure 21:
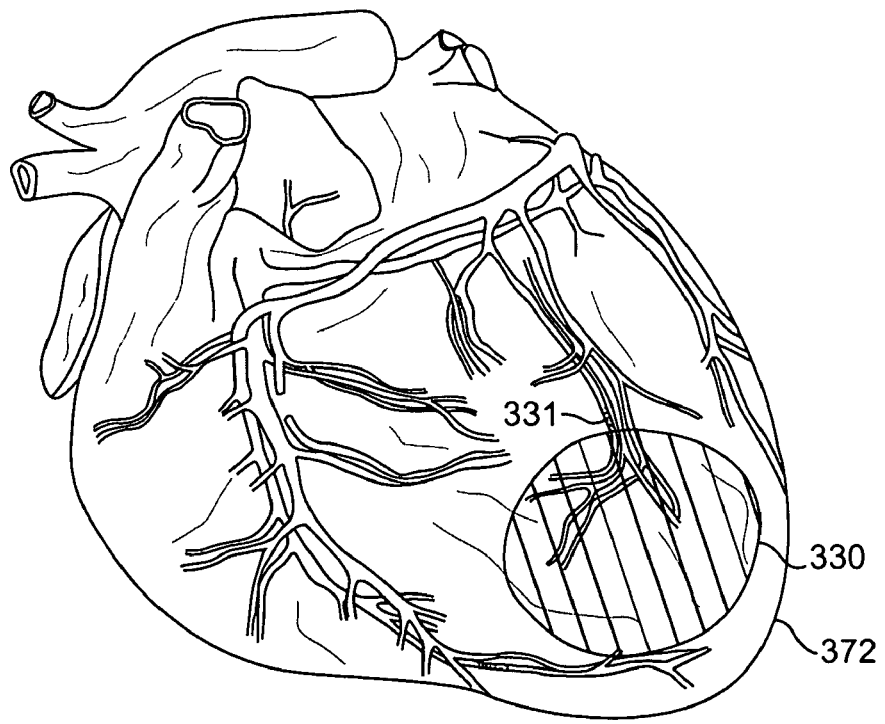
FIG. 21 is an anterior plan view of a heart in which occluding agent sites within the cardiac venous system lie in proximity to a aneurysm and in accordance with the Torrent-Guasp double loop concept.

While patterns of occluding agent sites are useful for treating localized conditions, one occluding agent site or a few isolated and unpatterned occluding agent sites established in proximity to a localized anomaly of the heart may also have therapeutic value. FIG. 21 shows a heart that has an aneurysm 330. In this example, occluding agent injected to form occluding agent site 331 may diffuse into the edges and body of the aneurysm 330. Where the diffusion is along the striations, the occluding agent site runs in parallel with the striations, hence along the vector of maximum contraction and relaxation, to provide maximum coupling of the healthy tissue of the myocardium with the aneurysm 330. While only one occluding agent site 331 is shown, multiple occluding agent sites in accordance with the teachings herein may be used if desired.

Occluding Agent Delivery Systems for Use in the Cardiac Venous System

Access to particular sections of the cardiac venous system is achieved in an manner suitable to the particular section being accessed. Many different types of injection systems known in the art may be adapted in ways that depend on the type of surgery (invasive or minimally invasive), the type of occlusion agent desired for use, and the pattern desired to be achieved by the injections. Injections may be made through a standard cannula placed directly into an epicardial cardiac vein during an open-chest procedure. Another technique applicable to a small part of the circulation is to access a section of an epicardial vein via a catheter that is floated in the coronary sinus. A more general technique uses a catheter that is placed through the femoral or jugular vein and then advanced under fluoroscopic guidance to the coronary sinus and into the coronary sinus and hence, the venous system of the heart. An adaptable catheter system for this purpose is the catheter system used in cardiology for the delivery of pacing leads for cardiac resynchronization therapy. The catheter can be used to visualize a specific site in the heart for the injection, thus making the injection as selective and regional as one desires it to be. The properties of the injection system are tailored for the size of the vein into which the agent is to be injected.

Figure 22A:
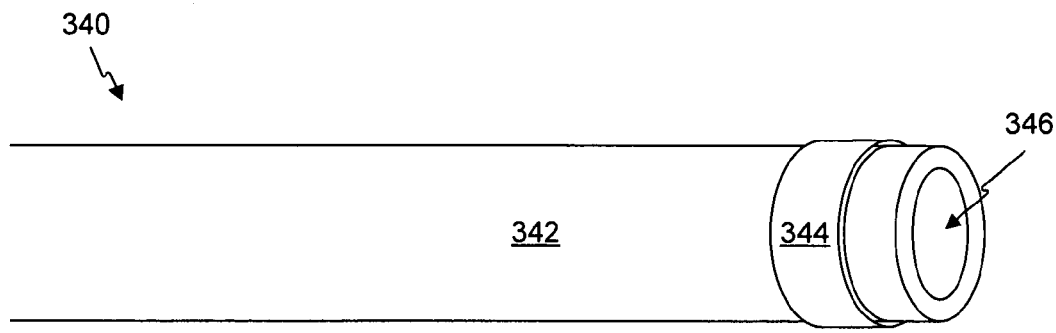
FIG. 22A is a side plan view of a catheter in a condition for being advanced through a cardiac vein.
Figure 22B:
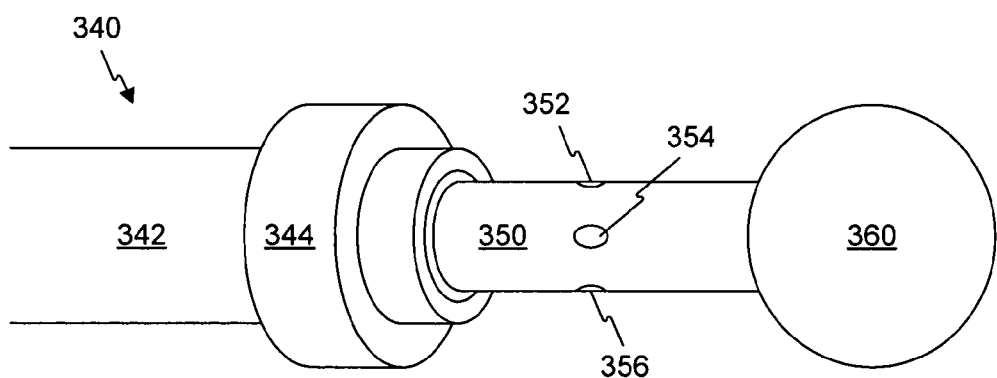
FIG. 22B is a side plan view of the catheter of FIG. 22A in a deployed condition.

A suitable catheter 340 for injecting occluding agent into the cardiac venous system is shown in various operating conditions in FIGS. 22A and 22B. FIG. 22A shows the catheter 340 in a condition suitable for being advanced through a cardiac vein, and FIG. 22B shows the catheter 340 in a deployed condition for defining a segment of a cardiac vein into which the occluding agent may be introduced. This illustrated implementation of the catheter 340 includes an outer tube 342 and an inner tube 350. The outer tube 342 defines a lumen 346 for communicating fluid and/or for communicating the inner tube 350 into the vein. The outer tube 342 and the inner tube 350 may be made from a variety of materials alone or in combination, including metals such as, for example, stainless steel or nitinol, and polymers such as polyethylene, nylon, and polyimide, among others.

The catheter 340 includes an expandable barrier 344, shown collapsed in FIG. 22A and expanded in FIG. 22B. The barrier 344 extends circumferentially around the outer tube 342 generally proximate the distal end thereof to block blood flow through the vein. The barrier 344 may be constructed of a variety of different materials, including, for example, Nylon, PEEK, and Pebax, among others. The outer tube 342 includes a lumen (not shown) to transmit fluid to/from the barrier 344 in order to inflate/deflate the barrier 344. With the barrier 344 in its collapsed position, the catheter 340 may be moved and positioned as desired within the cardiac venous system. When the catheter 340 is properly positioned, the barrier 344 is expanded to engage the wall of the vein, thereby stabilizing the distal end of the catheter 340, blocking blood flow through the vein, and establishing one end of the segment into which the occluding agent is to be introduced.

The inner tube 350 is slidably received within the lumen 346 for placing an occluder 360 within the vein in a fixed or variable spaced-apart relationship with the barrier 344. The occluder 360, which is removably disposed at the distal end of the inner tube 350, is passed through the lumen of the outer tube 342 in a collapsed condition, is advanced through the vein a desired distance from the distal end of the outer tube 342, and is expanded to engage the wall of the vein for establishing the other end of the segment into which the occluding agent is to be introduced. Although shown in FIG. 22B as being generally spherical as deployed, the occluder 360 may be any desired shape. The occluder 360 may be an inflatable balloon of any suitable material, such as, for example, nylon, polyamines, ethylene-vinyl acetate, polyvinyl chloride, olefin copolymers or homopolymers, polyethylenes, polyurethanes, and various blends of polymers and copolymers. Many different materials are suitable for expanding a balloon occluder by filling it, including, for example, hydrogels, silicones and epoxy, and various bioabsorbable materials such as hyaluronic acid injectable fillers, human collagens, and human fibrin sealant. Alternatively, the occluder 360 may be made of a suitable sponge material such as collagen that expands automatically when released into the vein, such materials being known to a person of ordinary skill in the art.

The inner tube 350 includes two lumen (not shown). One of these lumen is for transmitting fluid to/from the occluder 360 where the occluder 360 is designed to be inflatable and releasable, or inflatable and deflatable, or for containing a wire for mechanically releasing the occluder 360 where the occluder is designed to expand upon release, such as a sponge. Where the occluder is designed to expand upon release, the release wire and associated lumen may be eliminated if the release mechanism is triggered by the pressure of occluding agent injectate in the other lumen. The other lumen is for communicating fluid with ports 352, 354 and 356 (illustratively three ports are shown) on the inner tube 350. The ports 352, 354 and 356 are for introducing occluding agent into the between the occluder 360 and the barrier 344, and may be used to suction blood from the volume if desired.

To place occluding agent within a desired segment of the cardiac venous system, the catheter 340 as shown in FIG. 22A is advanced to a desired position within the cardiac venous system. The barrier 344 is expanded to stabilize the distal end of the catheter 340, to define one end of the segment, and to block the flow of blood to the heart from the segment. The inner tube 350 is advanced a desired distance into the vein from the distal end of the outer tube 342, and the occluder 360 is expanded to define the other end of the segment. Occluding agent is introduced into the segment through the ports 352, 354 and 356. The occluding agent is permitted to cure, and the inner tube 350 is retracted and removed from the catheter 340. The occluder 360 may be collapsed for withdrawal, or may be detached prior introduction of occluding agent, or may automatically detach as retraction of the inner tube 350 begins. The barrier 344 is collapsed and the catheter 340 is removed from the site. Optionally, a second occluder similar to the occluder 360 may be placed at the other end of the segment before the catheter 340 is removed.

Radiopaque materials may be disposed proximate the distal end of the outer tube 342 and/or the distal end of the inner tube 350 to facilitate or confirm proper placement of the distal end of the catheter 340 within the desired segment of the cardiac venous system.

The proximal ends (not shown) of the outer tube 342 and the inner tube 350 extend from the proximal end of the catheter 340 to allow the a physician to control the various functions performed by the catheter 340.

Occlusions and barriers may be formed from fast-setting or fast-curing occluding agent. Where the use of fast-setting occluding agent is desired, a catheter similar to the catheter 340 may be positioned with the inner tube extended. However, instead of the barrier 344 and the occluder 360, ports may be substituted for dispensing an occluding agent that is designed for rapidly solidification from a fluid state to a solid state. The rapid setting occluding agent may be dispensed into the vein segment from these ports to form two spaced-apart terminal occlusions, and a second occluding agent may be delivered into the vein segment between the spaced-apart occlusions to form a primary occlusion. The second occluding agent need not be rapid setting, and may be optimized for characteristics different than the rapid setting occluding agent used for the terminal occlusions. Moreover, the two terminal occlusions may be formed from different occluding agent, if desired. The materials used in the catheter should be selected to minimize bonding between the cured occluding agents and the catheter, to allow for withdrawal of the catheter. A suitable rapid-setting occluding agent is CoSeal® surgical sealant, which is available from Angiotech Pharmaceuticals of Vancouver, British Columbia, Canada, and Baxter Healthcare Corporation of Fremont, Calif.

The catheter 340 shown in FIG. 22, the variation using ports to dispense rapid setting occluding agent, and examples of other suitable catheters are described in greater detail in a U.S. Provisional Patent Application No. 61/123,700 filed Apr. 10, 2008, which names Hani N. Sabbah as inventor and is entitled "Method, Apparatus and Kits for Forming Structural Members Within the Cardiac Venous System," and which hereby is incorporated herein in its entirety by reference thereto.

Suitable Materials for Use in the Cardiac Venous System

Suitable material for use in the cardiac venous system for global resizing, global reshaping, both global resizing and reshaping, or localized treatment includes injectable agents, implantable devices, and combinations thereof. The material for the injected or implanted pattern and the dose (for an injectable agent), size and configuration (for an implantable device), and other material properties such as, for example, stiffness, malleability, elasticity, water absorption, and so forth, is selected based on the intended therapeutic effect. Where an injectable agent is used, the dose may be uniform, or if desired may change depending on such factors as the location within the pattern, the degree of support being sought, and the size of the vein at the site. Where implantable devices are used, devices of different cross-section may be used so that the effective cross-section may vary based on the size of the vein and the position in the pattern. Where the therapeutic effect is primarily resizing and reshaping, a suitable material preferably provides prompt structural support and may dissipate over time. Alginate, chitosan, fibrin glue, collagen, glycoaminoglycans, other biodegradable polymers including synthetic polymers, and hydrogel materials are illustrative of suitable materials for this purpose. Where long-term structural support is desired, the material preferably is resistant to absorption or breakdown by the body. Metals, polymers, silicone, and shaped memory materials are illustrative for this purpose. Where resizing, reshaping and reverse remodeling are desired, the material may be reabsorbed after providing some period of support and engineered so that it is replaced by myocytes, blood vessels, and so forth to provide the desired reverse remodeling. Injectable biopolymers in combination with cells such as fibroblasts, fibrocytes, stem cells, muscle cells, growth factor, stromal cell derived factor, or with other materials and/or cytokines that attract cells, or with both are suitable for this purpose.

Examples of suitable materials include natural and synthetic biologically-compatible polymers (any FDA approved polymer for human implantation), fibrin sealants, alginates, collagens, sugars, hydrogels, self-assembling peptides, PLGA, PEG, coagulation protein based sealants, hyaluronic acid, alginate and chitosan hydrogels and beads, alginate material with covalently attached peptides, alginate beads coated with chitosan material, self-assembling peptide scaffold hydrogels, and so forth, either alone or in combinations of two or more. Suitable biopolymer materials are commercially available from a variety of commercial sources, including the NovaMatrix Unit of FMC Biopolymer Corporation, 1735 Market Street, Philadelphia, Pa. 19103 and Omrix Biopharmaceuticals, 630 5th Avenue, 22nd Floor, New York, N.Y. 10111. Suitable materials also include mechanical devices made of metals, polymers (including plastics and silicone), shaped memory materials such as Nitonol, combinations of materials, and the like. Various materials are also described in U.S. Patent Application Publication 2005/0271631 published Dec. 8, 2005 in the name of Lee et al., which hereby is incorporated herein in its entirety by reference thereto. Other suitable materials include sugars such as monosaccharides, disaccharides, and trisaccharides. This list of material is illustrative, and essentially any FDA approved material may be used if it has a degree of purity, preparation time, ease of expression (viscosity), reaction rate (cure time), strength (energy to failure), compliance, water uptake, burst strength, tissue adherence, endurance, degradation rate, and so forth, that is suitable for forming a supportive structure upon injection or implantation into the selected venous segment.

Where injectable agents are used, the individual injections may be spaced to have essentially no linkage with one another, the therapeutic effect being achieved through the general thickening of the myocardial wall along the lines of the desired pattern. Alternatively, the injections may be more closely spaced, with the dose of the individual injections being related to the spacing between the injections to achieve a mechanical, chemical, or both mechanical and chemical linkage between the occluding agent sites, for realizing the therapeutic effect.

The structural material may serve as a platform for delivery of other therapeutic materials, including living cells (including, for example, myocytes, fibroblasts, fibrocytes or profibrotic blood progenitor cells, stem cells, and muscle cells), growth factors (including, for example, angiogenic factors such as VEGF, FGF, and HGF; chemotractants; stem cell derived factor; and TGF-b), stromal cell derived factor, stem cell products, peptides, proteins, genes, chondrocytes, insoluble molecules, other biologics, and so forth, alone or in combinations of two or more.

Generally, biocompatible polymers that are injectable into the cardiac veins as occluding agent are useful because they provide immediately a physical structure or filler that thickens the heart wall and thereby halts progression of remodeling, and in some cases reshapes and reverses remodeling; and administration is extremely flexible, ranging from minimally invasive techniques using catheters to open chest procedures. Additionally, they may also form matrices which for some polymers allows the delivery of therapeutic materials for in-situ tissue growth that promotes cell ingrowth for regeneration of functional tissue.

Regarding the first reason, the structural property of the biopolymer leads to points of decreased wall stress in the damaged heart chamber which in turn produce beneficial cardiac mechanics in addition to decreases in chamber dimensions. The desired decrease in cardiac wall stress is influenced both by the volume of biopolymer administered and by the stiffness of the material itself. With respect to volume, increasing total wall volume more than an incidental amount, illustratively about 4.5% or more, produces a significant, beneficial change in volume/pressure. With respect to stiffness, a non-contractile material with equal or slightly higher stiffness than myocardium is effective for decreasing wall stress (point fiber stress).

Desirable polymer properties for cardiac resizing and reshaping are as follows.

Origin/Purity. A suitable biopolymer may be synthetic, fully-defined, and consistent. Human- or animal-sourced polymers such as fibrin sealants, bovine collagens, and so forth are also suitable.

Sterility. Suitable biopolymers are sterile and suitable for presentation to the operating room both in syringes (open surgical application) and in catheters (less invasive procedures).

Thrombogenicity. Suitable material is non-thrombogenic.

Immunogenicity. To realize a simple mechanic effect, inert, nonimmunogenic materials are preferable. However, materials containing bioreactive peptides or proteins such as growth factors to induce tissue ingrowth can be very beneficial.

Preparation. Minimal handling such as thawing and pre-mixing is desirable. The product preferably is pre-filled or loaded onto both syringes (open surgery) and catheter systems (less invasive).

Administration/Gel Time: The polymerization or gelling characteristics of the biopolymer is dependent on the number of lines and the number of injections per line. For patterns that involve on the order of 20 injections (doses), the time period may be around 20 minutes. For patterns such as the single circumferential line that may involve as few as two or three injections and preferably no more than seven or eight injections, the time period is considerably shorter. The polymer may be delivered as a single mass or as microspheres.

Hardness/Density. We believe that the polymer should preferably have properties (stress strain relation) that make it somewhat stiffer that normal myocardium. Normal myocardium displays a fiber stress of 1-10 kPa.

Duration of Effect: The period for maintaining the supportive effect of the biopolymer has not been determined yet, but could be at least six months and, possibly, one year or longer.

Plasticity/Porosity. Porosity should be secondary to stiffness, concentration, or rate of degradation. However, a porosity of 300-420 µm may be adequate for cardiac tissue applications.

Biodegradation. Ideally, the material should degrade slowly in order to provide durable relief of wall stress, ventricular volume enhancement, reshaping, improvement of ejection fraction, and, in the long term, reversal of remodeling supported by native tissue re-growth. Illustratively, the substantial presence and function of the biopolymer should persist for at least six months and preferably longer.

Storage and Stability. Preferably the biopolymer may be stored at room temperature and is stable for 1 or 2 years.

Many different types of biocompatible polymers are suitable. Suitable fibrin sealants are available from a variety of manufacturers, such as Crosseal® and Quixil® Fibrin Sealant available from Ethicon Inc. of Sommerville, N.J., Omrix Pharmaceuticals of New York, N.Y., and Tisseel Fibrin Sealant available from Baxter Healthcare Corp. of Deerfield, Ill. A suitable fibrin glue may also be made from cryoprecipitate, which is a source of autologous fibrinogen prepared from a subject's own plasma. Other suitable polymers include synthetic resorbable self-curing hydrogel materials. One such material is DuraSeal® sealant, which is available from Confluent Surgical of Waltham, Mass. The DuraSeal sealant is a polyethylene glycol based sealant. Another such material is CoSeal® surgical sealant, which is available from Angiotech Pharmaceuticals of Vancouver, British Columbia, Canada, and Baxter Healthcare Corporation of Fremont, Calif. The CoSeal surgical sealant is made of two synthetic polyethylene glycols or PEGs, a dilute hydrogen chloride solution, and a sodium phosphate/sodium carbonate solution. At the time of administration, the mixed PEGs and solutions form a hydrogel that adheres to tissue. Both the DuraSeal and CoSeal sealants polymerize within seconds and are broken down in the body within weeks due to hydrolysis. Other suitable polymers include cyanoacrylate glues. Other suitable polymers include polyethylene oxides ("PEO"), PEO-poly-l-lactic acid ("PLLA-PEO block copolymer"), poly(N-isopropylacrylamide-co-acrylic acid) ("poly(NIPAAm-co-Aac)"), a pluronic agent, and poly-(N-vinyl-2-pyrrolidone) ("PVP"). Other suitable polymers include polysaccharides such as cellulose. A class of materials generally known as alginates are suitable polymers. Other suitable polymer include various beads and hydrogels which may be injected alone to mechanically disrupt neuronal signaling, or with other material to administer therapeutics along with mechanical disruption. The polymer-based beads and hydrogels may contain only polymer material, or may include cells such as stem cells, fibroblasts, or skeletal cells; proteins, plasmids, or genes; growth factors in either protein or plasmid form; chemo-attractants; fibrin factor (or fragment) E; RDG binding sites; various pharmaceutical compositions; neo-tissues; or other therapeutically beneficial materials; or any combination of the foregoing. Suitable polymers for beads and hydrogels include fibrin glue, collagen, alginates, and chitosan. Other suitable polymers include hyaluronic acid, sodium hyaluronate, and other formulations, Restylane Injectable Gel available from Q-Med of Scandinavia or from Medicis Aesthetics Holdings Inc., and Synvisc hyaluronic acid available from Gensyme. The polymer materials described herein generally illustrate certain broader classes of materials, which classes may contribute additional alternatives as would be apparent to one of ordinary skill. Where a compound is herein identified in relation to one or more embodiments described herein, precursors or analogs or derivatives thereof are further contemplated. For example, material structures that are metabolized or otherwise altered within the body to form such compound are contemplated. Or, combination materials that react to form such compound are also contemplated. Additional materials that are also contemplated are those which have molecular structures that vary insubstantial to that of such designated compounds, or otherwise have bioactivity substantially similar thereto with respect to the intended uses contemplated herein (e.g. removing or altering non-functional groups with respect to such bioactive function). Such group of compounds, and such precursors or analogs or derivatives thereof, is herein referred to as a "compound agent." Similarly, reference herein to other forms of "agents", such as for example "polymer agent" or "fibrin glue agent" may further include the actual final product, e.g. polymer or fibrin glue, respectively, or one or more respective precursor materials delivered together or in a coordinated manner to form the resulting material.

Self-gelling hydrogels are a suitable bio polymer. Such self-gelling hydrogels may be formed from alginate materials in the presence of divalent cations such $Ca^{2+}$, $Ba^{2+}$, $Mg^{2+}$, or $Sr^{2+}$. Gelling occurs when the divalent cations take part in ionic binding between blocks in the polymer chain, giving rise to a 3 dimensional network. In one approach, a dual chamber syringe converging into a single lumen injection needle may be used to inject the mixed components of the alginate mixture to gel in-vivo. One component may be a sodium alginate fully solublized in an aqueous solution such as $H_2O$. The other component may be one of the divalent cations mentioned above dispersed (preferably not dissolved) in solution. The compounds may be mixed in any suitable manner. Prior to injection, for example, a T-type adapter attached to the syringe may be set to provide mixing of the components and initiate the gelling action, and then set to allow the alginate mixture undergoing gelling to enter the lumen and to be injected into the cardiac tissue of interest. The alginate mixture may be injected immediately, or may be allowed to partially pre-cure in the syringe in order to increase the viscosity of the hydrogel prior to injection. In some instances, a pre-cured formulation may reduce the possibility that a less viscous hydrogel may diffuse or migrate away from the tissue area of interest after injection. In order to limit or minimize diffusion/migration away from the injection site, it may be beneficial to utilize alginate materials with molecular weights in excess of 300,000. In another approach, the sodium alginate solution and dispersed cation may be pre-mixed in an external mixing chamber, and aspirated into a single lumen syringe from which it may be injected into the cardiac tissue of interest. In another approach, the sodium alginate solution may be pre-mixed with an appropriate peptide (e.g., RGD or GREDVY) for covalent attachment of the peptide to the alginate prior to mixing with the divalent cations.

Advantageously, the material properties of ionically cross-linked alginate hydrogels may be controlled in various ways. Techniques that vary the molecular weight distribution for controlling and decoupling the viscosity of the pre-gel solution from the post-gel stiffness are disclosed in H. Kong et al., Controlling material properties of ionically cross-linked alginate hydrogels by varying molecular weight distribution, Mat. Res. Soc. Symp. Proc., Vol. 711, 2002, pages GG5.7.1-GG5.7.4, which hereby is incorporated herein in its entirety by reference thereto. Other techniques, some of which are applicable to polyethylene glycol or PEG materials, are disclosed in U.S. Pat. No. 6,566,406 issued May 20, 2003 to Pathak et al., U.S. Pat. No. 6,887,974 issued May 3, 2005 to Pathak, and US Patent Application Publication No. 2004/0023842 published Feb. 5, 2004 in the name of Pathak et al., all of which hereby are incorporated herein in their entirety by reference thereto.

An example of an injectable cross-linked polymeric preparation is disclosed in US Patent Application Publication No. 2006/0083721 published Apr. 20, 2006 in the name of Cohen et al., and in US Patent Application Publication No. 2005/0003010 published Jan. 6, 2005 in the name of Cohen et al., all of which hereby are incorporated herein in their entirety by reference thereto.

U.S. Pat. No. 6,063,061 issued May 16, 2000 to Wallace et al., which hereby is incorporated herein in its entirety by reference thereto, discloses the application of molecular gels to target sites in a patient's body by extruding the gel through an orifice at the target site. Wallace et al. considered the effect of the extent of cross-linking of the polymer on several functional properties of the hydrogel including extrudability, absorptiveness of surrounding biological fluids, cohesiveness, ability to fill space, swelling ability and ability to adhere to the tissue site. The extent of cross-linking of the polymeric gel composition may be controlled by adjusting the concentration of cross-linking agent, controlling exposure to cross-linking radiation, changing the relative amounts of mono- and poly-unsaturated monomers, varying reaction conditions, and the like. Moreover, properties may also be varied by mechanically disrupting the hydrogels to create multiple subunits of hydrogel having a size which enhances the ability to fill and pack a space to which it is being delivered.

US Patent Application Publication No. 2003/0211793 published Nov. 13, 2003 in the name of Bell et al., which hereby is incorporated herein in its entirety by reference thereto, discloses an injectable bio-compatible material that comprises a biopolymer fiber that is assembled from biopolymer fibrils whose axes are substantially parallel with the axis of the fiber.

Another example of a occluding agent is the polysaccharide sponge, examples of which are disclosed in U.S. Pat. No. 6,334,968 issued Jan. 1, 2002 to Shapiro et al., and in U.S. Pat. No. 6,425,918 issued Jul. 30, 2002 to Shapiro et al., which hereby are incorporated herein in their entirety by reference thereto.

Another suitable therapeutic agent is alginate beads coated with chitosan material, which is particularly suitable in cases where it may be desired to anchor the alginate beads to the immediate area of injection. In this case it may be desirable to overcoat the alginate beads with a coating both chemically attached to the alginate surface on the inboard side of the coating and simultaneously bonded to myocardial tissue on the outboard. Given that both the alginate surface and the myocardial tissue have negative bonding sites available, an overcoat with a positive charge density may be appropriate. Chitosan is such a material. Chitosan is a linear polysaccharide, and given its positive charge density is a bioadhesive which readily binds to negatively charged surfaces such as mucosal membranes. The chitosan overcoat may be applied by dip coating or other known procedures, wherein the chitosan may ionically bond to the available negative sites on the alginate surface. Given this, the chitosan may act as an anchor to immobilize the beads to the negatively charged myocardial tissue, giving temporary mechanical integrity at the injection site. Temporary, in the sense that the chitosan overcoat will eventually be enzymatically dissolved. "Anchoring time" may be prolonged by increasing the thickness of the chitosan overcoat. Beads and hydrogels are described in U.S. patent application Ser. No. 11/818,220 filed Jun. 13, 2007 in the name of Lee et al., and in U.S. Patent Application Ser. No. 60/813,184 filed Jun. 13, 2006 in the name of Lee et al., which are hereby incorporated herein in their entirety by reference thereto.

The properties of injectable materials may be adjusted in view of the characteristics of the venous system (diameter and distensibility) to occupy space so as to enhance thickening of the wall, or to enhance linkage between occluding agent sites.

Implantable mechanical devices such as particles, rods, spheres, expandable small balloons, and struts may also be used as occluding agent. US Patent Application Publication No. 2005/0080402 published Apr. 14, 2005 in the name of Santamore et al., which hereby is incorporated herein in its entirety by reference thereto, discloses various implantable devices for stiffening the myocardium. Mechanical struts may be made of stainless steel, titanium, or other known biocompatible metals or other rigid materials, may be long or short in length, and may be implanted by techniques well known in the field of cardiac surgery. One instrument suitable for use in creating channels into which struts may be introduced uses a laser to form a channel in the wall of a patient's heart. This channel may be used to provide access for implanting a mechanical strut of the type discussed above. A suitable instrument is disclosed in U.S. Pat. No. 6,132,451 issued Oct. 17, 2000 to Payne et al., which hereby are incorporated herein in their entirety by reference thereto. Implantable mechanical devices may also be drug-eluting to administer further treatment.

Injectates and implants that swell after being placed in the venous system are effective to enhance wall thickening without complicating administration. In particular, trauma from the injection or implantation may be minimized. Swellable polymers may be used. Moreover, firm objects such as microspheres and rods that are made of a swellable polymer which expand after implantation or injection into the myocardium may be designed for a specific expansion size, which allows for fine control over occlusion of the vein and the degree of thickening of the heart wall. The speed of expansion may be controlled to manage disruption.

Rapidly growing cells and rapid growth-promoting biologics may also be used as occluding agent, whether natural or genetically manipulated.

Animal Studies

A study was undertaken on two normal dogs to understand the effects of direct injections of alginate into the venous system of the heart. Each of two mongrel dogs received an injection of alginate into their cardiac veins; specifically, dog 07-105 received an injection of approximately three milliliters of a self-gelling alginate into a left ventricular superficial cardiac anterior vein, and dog 07-106 received an injection of approximately three milliliters of a self-gelling alginate into a left ventricular superficial cardiac posterior vein. The alginate formulation used was a Ca-Alginate/Na-Alginate formulation available from the NovaMatrix Unit of FMC Biopolymer Corporation, 1735 Market Street, Philadelphia, Pa. 19103. The vein was blocked with a suture, and the alginate was injected through the wall of the vein.

Left Ventricular wall thickness, left ventricular end diastolic volume ("EDV") and end systolic volume ("ESV"), and left ventricular ejection fraction ("EF") were measured pre-treatment and post-treatment, where post-treatment was two weeks after the injection. The measurements are shown below in Tables 1, 2, 3 and 4 respectively. For dog 07-105 which received an alginate injection into a cardiac anterior vein, the anterior wall thickness increased 7.4% while the thicknesses of the septal wall and the posterior wall were essentially unchanged at −1.0% and −0.8% respectively. For dog 07-106 which received an alginate injection into a cardiac posterior vein, the posterior wall thickness increased 7.0% while the thicknesses of the septal wall and the anterior wall were essentially unchanged at 0.0% and −0.9% respectively. As expected, the cardiac wall receiving treatment thickened while the other cardiac walls did not. However, the wall thickening did not affect the performance of the healthy heart, in which end diastolic volume, end systolic volume, and ejection fraction were essentially unchanged. This study indicates that when injected into a superficial vein, alginate enters into the network of veins that course through the cardiac muscle without significantly injuring the heart muscle in proximity to the vein or degrading the normal contraction of the heart muscle.

TABLE 1

WALL THICKNESS (cm)

| ES Wall Thickness (cm) | Pre-Treatment | Post-Treatment | Change (%) |
| --- | --- | --- | --- |
| Anterior Wall 07-105 | 1.13 | 1.22 | 7.4 |
| Anterior Wall 07-106 | 1.12 | 1.11 | −0.9 |
| Septal Wall 07-105 | 0.99 | 0.98 | −1.0 |
| Septal Wall 07-106 | 1.02 | 1.02 | 0.0 |
| Posterior Wall 07-105 | 1.25 | 1.24 | −0.8 |
| Posterior Wall 07-106 | 1.07 | 1.15 | 7.0 |

TABLE 2

END DIASTOLIC VOLUME (EDV - ml)

| Dog # | Pre-Treatment | 2 Weeks |
| --- | --- | --- |
| 07-105 | 57 | 58 |
| 07-106 | 51 | 50 |
| Mean | 54 | 54 |
| STD | 4.2 | 5.7 |

TABLE 3

END SYSTOLIC VOLUME (ESV - ml)

| Dog # | Pre-Treatment | 2 Weeks |
| --- | --- | --- |
| 07-105 | 30 | 32 |
| 07-106 | 22 | 19 |
| Mean | 26 | 25.5 |
| STD | 5.7 | 9.2 |

TABLE 4

EJECTION FRACTION (EF - %)

| Dog # | Pre-Treatment | Post-Treatment |
| --- | --- | --- |
| 07-105 | 47 | 45 |
| 07-106 | 57 | 62 |
| Mean | 52 | 54 |
| STD | 7.1 | 12.0 |

Figure 23:
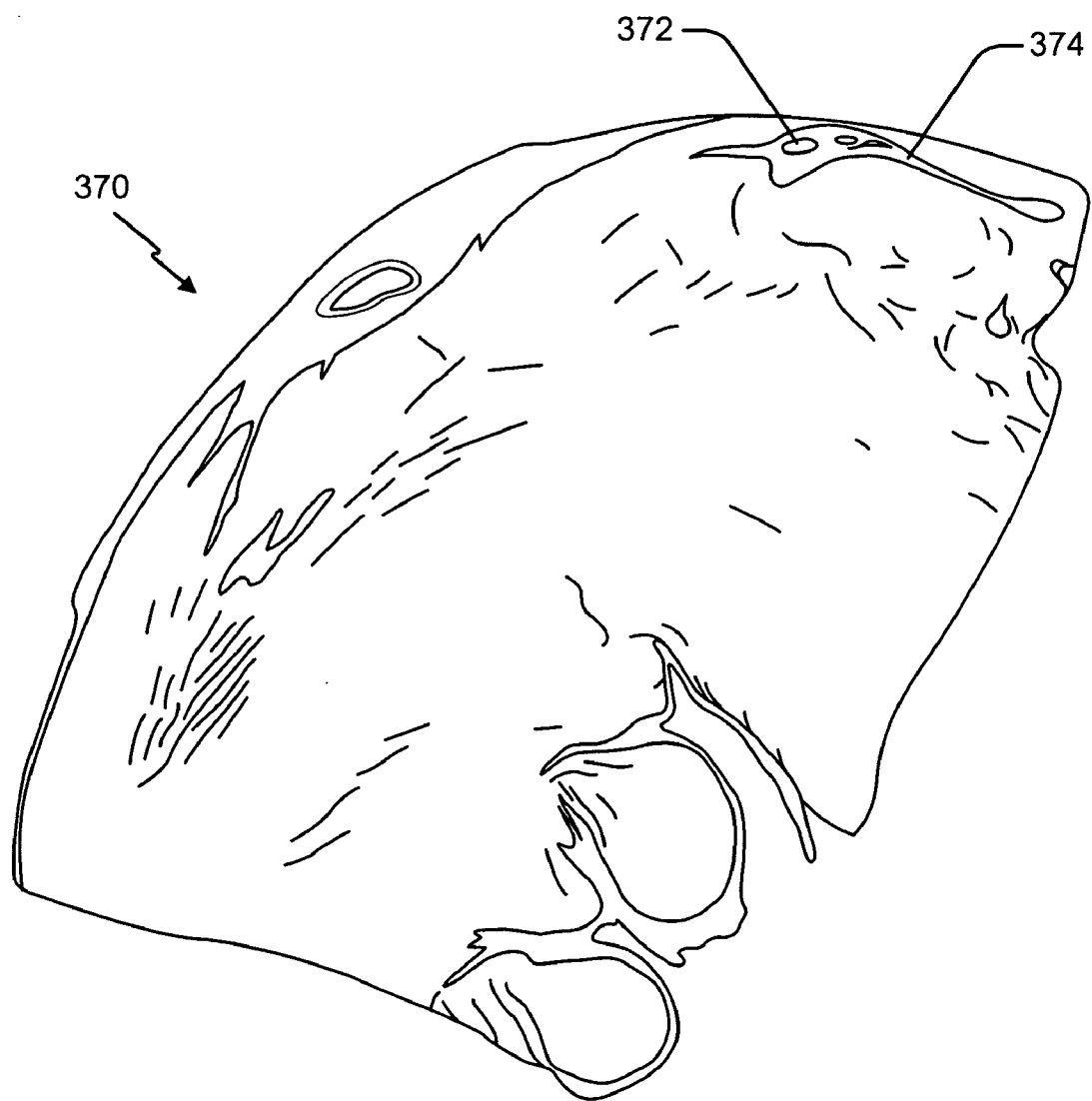
FIG. 23 is a micrograph of a transmural section of the left ventricle anterior wall of the heart.
Figure 24:
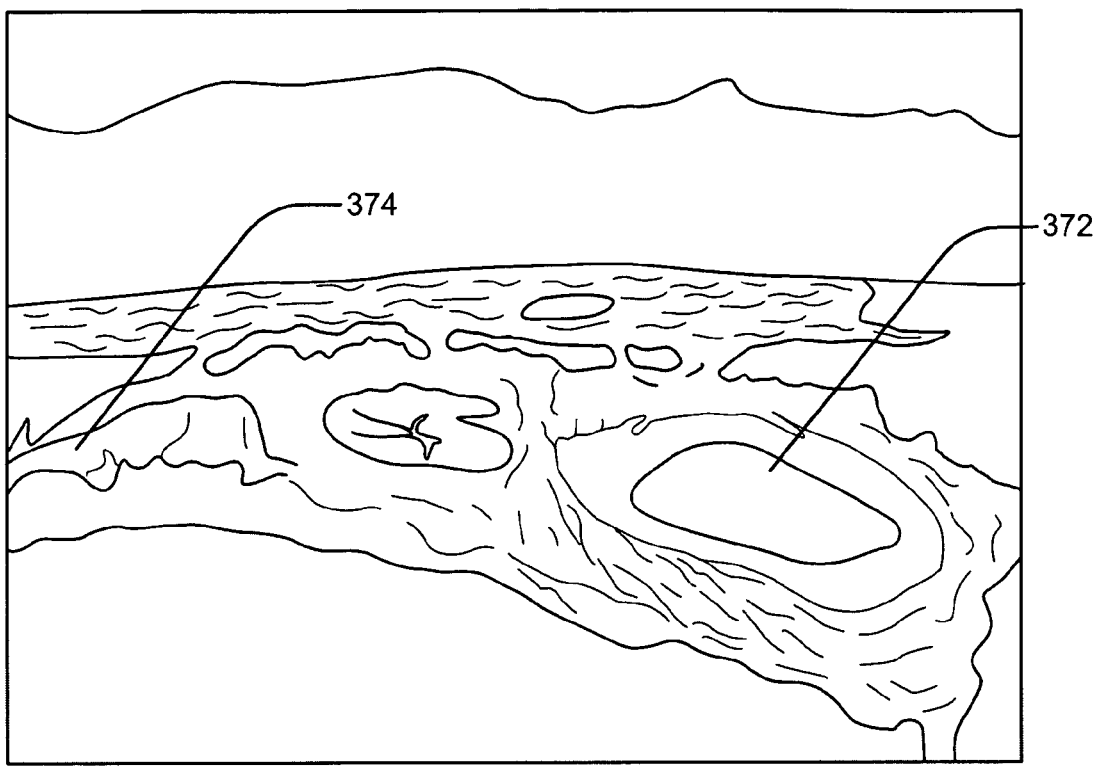
FIG. 24 is a 4× enlarged view of a first part of the heart section of FIG. 23.
Figure 25:
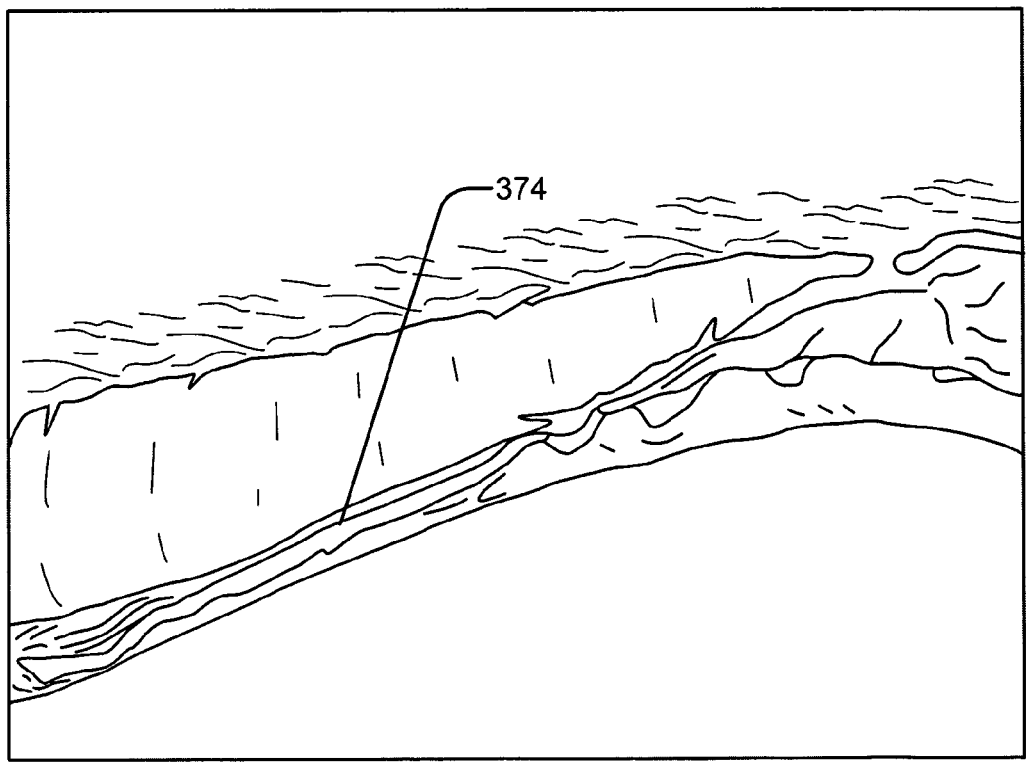
FIG. 25 is a 4× enlarged view of a second part of the heart section of FIG. 23.
Figure 26:
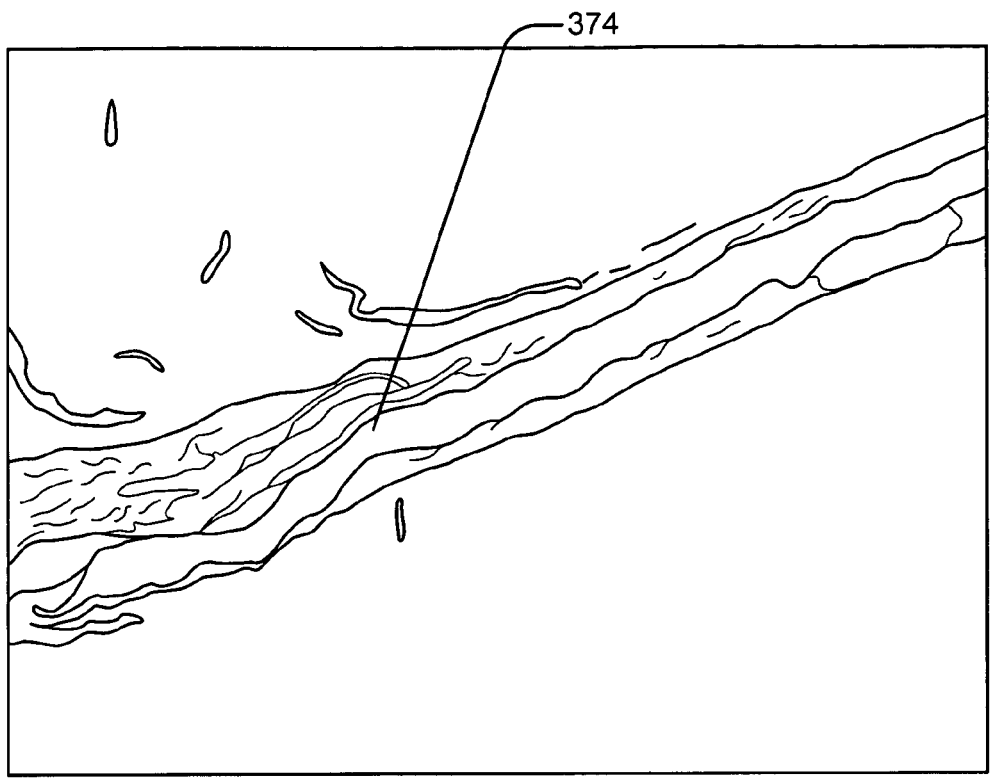
FIG. 26 is a 10× enlarged view of the second part of the heart section of FIG. 23.
Figure 27:
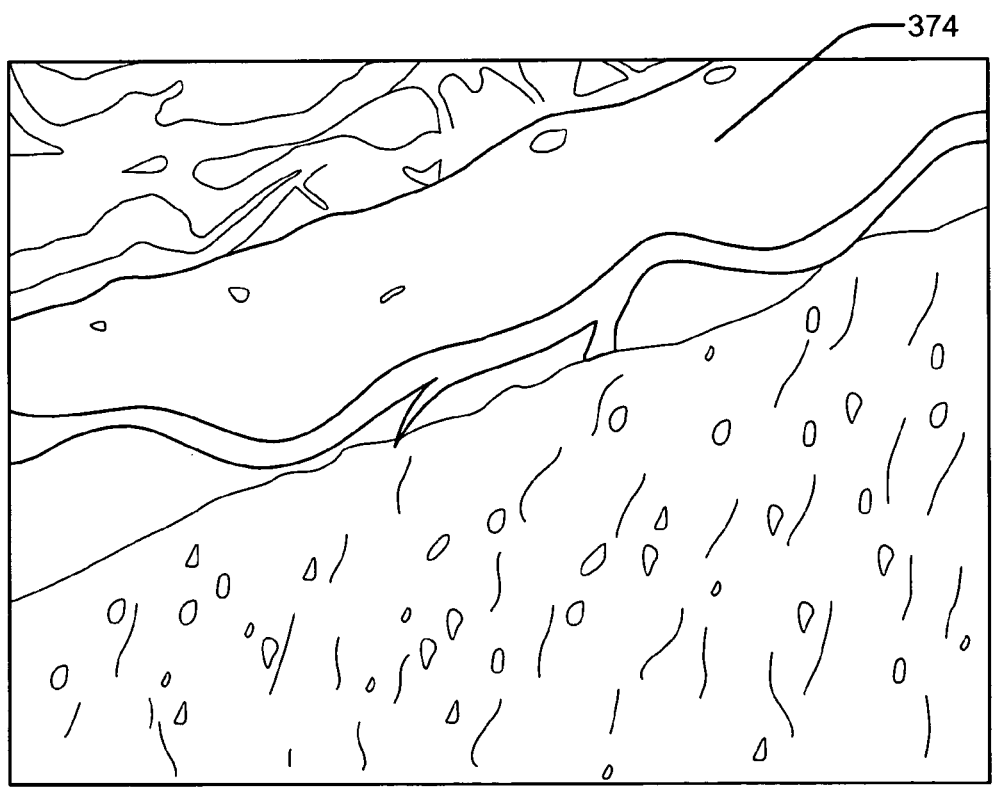
FIG. 27 is a 40× enlarged view of the second part of the heart section of FIG. 23.

Images of the heart for dog 07-105 in which alginate was injected into a cardiac anterior vein are shown in FIGS. 23-27. FIG. 23 shows a normal micrograph of a transmural section 370 of the left ventricle anterior wall of the heart that was prepared for histologic examination using Masson's Trichrome Stain. The appearance was normal. A coronary artery 372 is visible in a plane normal to its axis, and a proximate vein 374 is visible in a plane along its axis. FIG. 24 shows an enlarged view (objective×4) of a part of the heart section of FIG. 23 that contains the coronary artery 372, and part of a proximate vein 374 that contains alginate. FIG. 25 shows an enlarged view (objective×4) of an adjacent part of the heart section which contains another part of the elongated cardiac vein 374, in which the alginate mass filling the vein 374 is clearly visible. FIG. 26 is an enlargement (objective× 10) of a part of FIG. 25, and shows that normal tissue surrounds a part of the elongated cardiac vein filled with the alginate. FIG. 27 is a further enlargement (objective×40) of a part of heart that contains the elongated cardiac vein 374 and was prepared for histologic examination using H&E Stain. The alginate fills the vein 374, which is surrounded by tissue that appears normal.

Another study was undertaken to understand the effects of direct injections of alginate into the venous system of the heart on the progression of left ventricular dysfunction and remodeling in dogs with heart failure. Two mongrel dogs received multiple sequential intracoronary embolizations with polystyrene latex microspheres 77-102 um in diameter, to achieve an LV ejection fraction equal to or less than thirty-five percent. Two weeks after the last embolization, the dogs received alginate injections directly into both a superficial cardiac anterior vein and a superficial cardiac posterior vein. Each injection was three milliliters, which was sufficient to distend the veins. The alginate formulation used was a self-gelling Ca-Alginate/Na-Alginate formulation available from the NovaMatrix Unit of FMC Biopolymer Corporation, 1735 Market Street, Philadelphia, Pa. 19103. The vein was blocked with a suture, and the alginate was injected through the wall of the vein.

The thicknesses of the anterior wall, the septal wall, and the posterior wall were measured pre-treatment and 30 minutes after the injection. The measurements are shown below in Table 5. The degree of thickening attributable to the alginate injections was significant for both dogs. For dog 07-104 the anterior and posterior walls thickened by 9.7% and 9.1% respectively, while for dog 07-114 the anterior and posterior walls thickened by 6.2% and 10.9% respectively.

TABLE 5

WALL THICKNESS (cm)

| ES Wall Thickness (cm) | Pre-Treatment | Post-Treatment | Change (%) |
|---|---|---|---|
| Anterior Wall 07-104 | 1.21 | 1.34 | 9.7 |
| Anterior Wall 07-114 | 0.91 | 0.97 | 6.2 |
| Septal Wall 07-104 | 0.92 | 0.93 | 1.1 |
| Septal Wall 07-114 | 0.98 | 0.97 | −1.0 |
| Posterior Wall 07-104 | 1.2 | 1.32 | 9.1 |
| Posterior Wall 07-114 | 0.98 | 1.1 | 10.9 |

Figure 28:
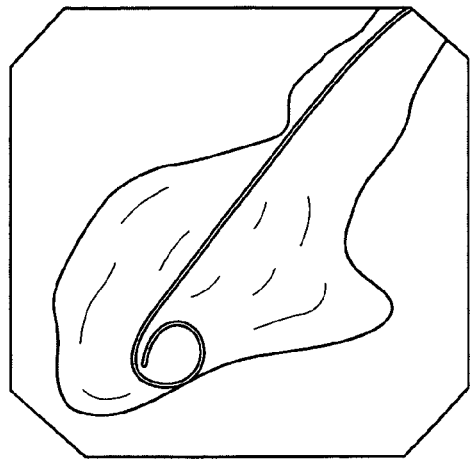
FIG. 28 is a ventriculograph of a pretreatment heart in end-diastole.
Figure 29:
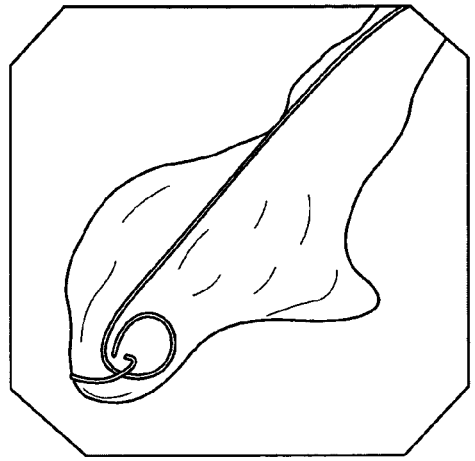
FIG. 29 is a ventriculograph of a pretreatment heart in end-systole.
Figure 30:
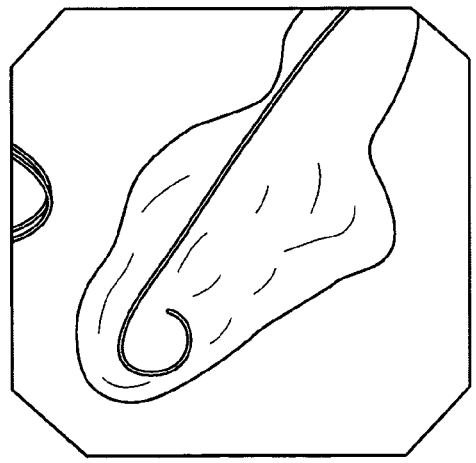
FIG. 30 is a ventriculograph of a postreatment heart in end-diastole.
Figure 31:
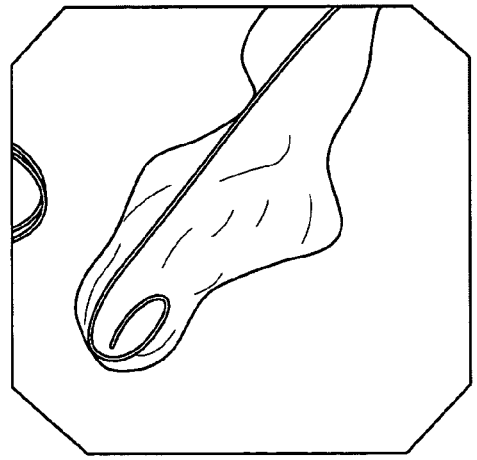
FIG. 31 is a ventriculograph of a postreatment heart in end-systole.

The improvements are visible in the ventriculographs of dog 07-104 shown in FIGS. 28-31. FIGS. 28 and 29 show pretreatment end-diastole and end-systole respectively, and FIGS. 30 and 31 show 2 week postreatment end-diastole and end-systole respectively. After two weeks, the animals treated by injection of alginate into the superficial veins, namely dogs 07-104 and 07-114, showed an improvement of ESV, namely a reduction of ESV with no change in EDV, and a substantial improvement or increase in EF. The improvements are believed to result from increased thickness of the ventricular wall at sites of vein injection. The results are shown below in TABLES 7-9.

TABLE 7

END DIASTOLIC VOLUME (EDV-ml)

| Dog # | Base | Pre-Treatment | 2 Weeks | 6 Weeks | Post-Treatment |
|---|---|---|---|---|---|
| 07-104 | 50 | 63 | 64 | 63 | 64 |
| 07-114 | 43 | 48 | 47 | 48 | 49 |
| Mean | 47 | 56 | 56 | 56 | 57 |
| STD | 4.9 | 10.6 | 12.0 | 10.6 | 10.6 |

TABLE 8

END SYSTOLIC VOLUME (ESV-ml)

| Dog # | Base | Pre-Treatment | 2 Weeks | 6 Weeks | Post-Treatment |
|---|---|---|---|---|---|
| 07-104 | 24 | 40 | 32 | 32 | 30 |
| 07-114 | 18 | 30 | 27 | 28 | 28 |
| Mean | 21 | 35 | 30 | 30 | 29 |
| STD | 4.2 | 7.1 | 3.5 | 2.8 | 1.4 |

TABLE 9

EJECTION FRACTION (EF-%)

| Dog # | Base | Pre-Treatment | 2 Weeks | 6 Weeks | Post-Treatment |
|---|---|---|---|---|---|
| 07-104 | 52 | 37 | 50 | 49 | 53 |
| 07-114 | 58 | 38 | 43 | 42 | 43 |
| Mean | 55 | 38 | 47 | 46 | 48 |
| STD | 4.2 | 0.7 | 4.9 | 4.9 | 7.1 |

This study indicates that alginate may be injected into a cardiac vein and is effective to thicken the muscular heart wall, and is effective to treat local anomalies or to resize and reshape the heart if injected in a suitable pattern and in doing so, improve the pumping function of the heart.

The description of the invention including its applications and advantages as set forth herein is illustrative and is not intended to limit the scope of the invention, which is set forth in the claims. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein, including of the alternatives and equivalents of the various elements of the embodiments, may be made without departing from the scope and spirit of the invention.

The invention claimed is:

1. A method of treating a heart having a myocardium and a cardiac venous system, comprising:
    identifying a plurality of segments of the cardiac venous system that are disposed along a therapeutically beneficial global pattern, the pattern being for treatment of dilated cardiomyopathy or congestive heart failure, and each of the segments comprising venules disposed within the myocardium forming an occlusion at each end of each of the segments; and
    introducing a biocompatible occluding agent into the segments of the cardiac venous system in a therapeutically effective amount to establish a plurality of respective discrete masses in the segments and venules for thickening and relieving stress in the myocardium of the heart along the pattern, and reducing systolic volume within a chamber of the heart wherein the introducing step comprises injecting the biocompatible occluding agent into the segments between the respective occlusions thereof to form the discrete masses.

2. The method of claim 1 wherein the pattern is a global pattern for treatment of a chamber of the heart by reshaping the chamber.

3. The method of claim 1 wherein the pattern is a global pattern for treatment of a left ventricle.

4. The method of claim 3 wherein the pattern essentially consists of a line that circumferentially spans across at least most of a free wall of the left ventricle proximate to a widest part of the free wall.

5. The method of claim 4 wherein the plurality of discrete masses in the pattern is from three to nine.

6. The method of claim 5 wherein the plurality of discrete masses in the pattern is from six to seven.

7. The method of claim 3 wherein the pattern essentially consists of a plurality of lines that circumferentially span across at least most of a free wall of the left ventricle.

8. The method of claim 3 wherein the pattern comprises a line that longitudinally spans across at least most of a free wall of the left ventricle.

9. The method of claim 8 wherein the plurality of discrete masses in the pattern is from three to seven.

10. The method of claim 9 wherein the plurality of discrete masses in the pattern is from four to six.

11. The method of claim 3 wherein the pattern essentially consists of a plurality of lines that longitudinally span across at least most of a free wall of the left ventricle.

12. The method of claim 3 wherein the pattern comprises:
a line that circumferentially spans across at least most of a free wall of the left ventricle; and
a line that longitudinally spans across at least most of a free wall of the left ventricle.

13. The method of claim 1 wherein:
the biocompatible occluding agent is injectable; and
the introducing step comprises injecting the biocompatible occluding agent into the segments of the cardiac venous system.

14. The method of claim 13 wherein the biocompatible occluding agent comprises a non-living material.

15. The method of claim 14 wherein the non-living material is a polymer.

16. The method of claim 14 wherein the biocompatible occluding agent further comprises living cells, growth factors, peptides, proteins, or any combination thereof.

17. The method of claim 13 wherein the biocompatible occluding agent comprises particulate material.

18. The method of claim 1 wherein the occluding agent is implantable.

19. The method of claim 1 wherein the occluding agent comprises drug-eluting material.

20. The method of claim 1 wherein:
the biocompatible occluding agent comprises an injectable alginate hydrogel; and
the introducing step comprises injecting the alginate hydrogel into the segments of the cardiac venous system to form the discrete masses.

21. The method of claim 1 further comprising:
forming an occlusion at one end of each of the segments;
wherein the biocompatible occluding agent is injectable; and
wherein the introducing step comprises injecting the biocompatible occluding agent into the segments adjacent the respective occlusions to form the discrete masses.

22. A method of treating a dilated left ventricle in a heart of a patient, comprising:
identifying a plurality of segments of the cardiac venous system that are disposed in a therapeutically beneficial global pattern along a free myocardial wall of the left ventricle, and also disposed in anterior, anterior lateral, and posterior lateral regions of the heart, the pattern being for treatment of dilated cardiomyopathy or congestive heart failure, and each of the segments comprising venules disposed within the free myocardial wall of the left ventricle;
forming an occlusion at each end of the each of the segments;
injecting doses of biocompatible polymer agent into the segments between the respective occlusions thereof to form respective stress-reducing structures, each of the structures being disposed in a respective one of the segments and extending into the venules thereof;
the stress-reducing structures being distributed in the anterior, anterior lateral, and posterior lateral regions of the heart with essentially no linkage with one another, for globally reducing stress in the free myocardial wall of the left ventricle along the pattern; and
the doses being in amounts effective for thickening the free myocardial wall of the left ventricle, reducing systolic volume of the left ventricle, and improving function of the left ventricle.

23. The method of claim 22 wherein the segments are disposed in a first circumferential line along the free myocardial wall of the left ventricle.

24. The method of claim 23 wherein the first circumferential line is at a near widest part of the left ventricle, and the segments are disposed only in the first circumferential line.

25. The method of claim 24 wherein at least five segments are in the first circumferential line and are evenly distributed.

26. The method of claim 24 wherein at least five segments are in the first circumferential line and are unevenly distributed.

27. The method of claim 22 wherein the segments are disposed in a first circumferential line and in a second circumferential line along the free myocardial wall of the left ventricle, the first and second circumferential lines being generally parallel to and spaced-apart from one another.

28. The method of claim 22 wherein the segments are disposed in a first circumferential line, in a second circumferential line, and in a third circumferential line along the free myocardial wall of the left ventricle, the first, second and third circumferential lines being generally parallel to and spaced-apart from one another.

29. The method of claim 22 wherein the segments are disposed in three longitudinal lines along the free myocardial wall of the left ventricle, from base to apex of the heart.

30. The method of claim 29 wherein at least four segments are in each of the longitudinal lines and are evenly distributed.

31. The method of claim 29 wherein at least four segments are in each of the longitudinal lines and are unevenly distributed.

32. The method of claim 22 wherein the biocompatible occluding agent comprises a polymer agent.

33. The method of claim 32 wherein the polymer agent comprises an alginate hydrogel.

34. The method of claim 32 wherein the polymer agent comprises polyethylene glycol.

35. The method of claim 32 wherein the polymer agent comprises a polymer in combination with living cells, growth factors, peptides, proteins, or any combination thereof.

36. The method of claim 23 wherein the segments are further disposed in three longitudinal lines along the free myocardial wall of the left ventricle, from base to apex of the heart.

37. A method of treating a dilated left ventricle in a heart of a patient, comprising:
identifying a plurality of segments of the cardiac venous system that are disposed in a circumferential line along a free myocardial wall of the left ventricle and at a near widest part of the left ventricle, and also disposed in anterior, anterior lateral, and posterior lateral regions of the heart, each of the segments comprising venules disposed within the free myocardial wall of the left ventricle;
forming an occlusion at each end of each of the segments;

injecting doses of biocompatible alginate hydrogel agent into the segments between the respective occlusions thereof to form respective stress-reducing structures, each of the structures being disposed in a respective one of the segments and extending into the venules thereof;

the stress-reducing structures being distributed in the anterior, anterior lateral, and posterior lateral regions of the heart with essentially no linkage with one another, for globally reducing stress in the free myocardial wall of the left ventricle along the circumferential line; and the doses being in amounts effective for thickening the free myocardial wall of the left ventricle, reducing systolic volume of the left ventricle, and improving function of the left ventricle.

* * * * *

UNITED STATES PATENT AND TRADEMARK OFFICE
CERTIFICATE OF CORRECTION

| | | |
|---|---|---|
| PATENT NO. | : 7,875,017 B2 | |
| APPLICATION NO. | : 12/082368 | |
| DATED | : January 25, 2011 | |
| INVENTOR(S) | : Hani N. Sabbah | |

It is certified that error appears in the above-identified patent and that said Letters Patent is hereby corrected as shown below:

In column 26, line 32, cancel the text beginning with "1. A method of" to and ending "discrete masses." in column 26, line 50, and insert the following claim:

1. A method of treating a heart having a myocardium and a cardiac venous system, comprising:

identifying a plurality of segments of the cardiac venous system that are disposed along a therapeutically beneficial global pattern, the pattern being for treatment of dilated cardiomyopathy or congestive heart failure, and each of the segments comprising venules disposed within the myocardium;

forming an occlusion at each end of each of the segments; and introducing a biocompatible occluding agent into the segments of the cardiac venous system in a therapeutically effective amount to establish a plurality of respective discrete masses in the segments and venules for thickening and relieving stress in the myocardium of the heart along the pattern, and reducing systolic volume within a chamber of the heart wherein the introducing step comprises injecting the biocompatible occluding agent into the segments between the respective occlusions thereof to form the discrete masses.

Signed and Sealed this
Third Day of May, 2011

David J. Kappos
*Director of the United States Patent and Trademark Office*